United States Patent
Nakayama et al.

Patent Number: 5,532,267
Date of Patent: Jul. 2, 1996

[54] AMIDINONAPHTHYL FURANCARBOXYLATE DERIVATIVES AND ACID ADDITION SALTS THEROF

[75] Inventors: Toyoo Nakayama, Funabashi; Seizo Taira, Chiba; Hiroyuki Kawamura, Ichikawa; Masaoki Shibuya, Chiba; Masahiro Iwaki, Ichikawa, all of Japan

[73] Assignee: Torii & Co., Ltd., Tokyo, Japan

[21] Appl. No.: 215,785

[22] Filed: Mar. 22, 1994

Related U.S. Application Data

[63] Continuation-in-part of Ser. No. 956,287, Oct. 5, 1992, abandoned.

[30] Foreign Application Priority Data

Feb. 10, 1992 [JP] Japan ................................ 4-023848

[51] Int. Cl.$^6$ ..................... A61K 31/335; A61K 31/34; C07D 307/46; C07D 317/14
[52] U.S. Cl. .................. 514/467; 514/471; 549/229; 549/484; 549/492; 549/493; 549/494; 549/495
[58] Field of Search ................... 514/467, 471; 549/229, 484, 492, 493, 494, 495

[56] References Cited

U.S. PATENT DOCUMENTS

| | | | |
|---|---|---|---|
| 4,563,527 | 1/1986 | Fujii et al. | 546/169 |
| 4,634,783 | 1/1987 | Fujii et al. | 549/475 |

*Primary Examiner*—Ba Kim Trinh
*Attorney, Agent, or Firm*—Beveridge, DeGrandi, Weilacher & Young

[57] ABSTRACT

Amidinonaphthyl furancarboxylate derivatives of the formula I

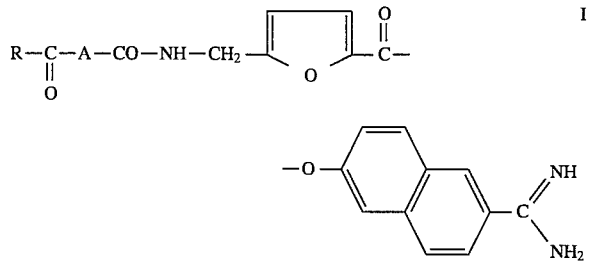

wherein A is a single bond or A denotes (a) a phenyl group, cyclopentyl group, or cyclohexyl group, (b) an alkenylphenyl group, alkylphenyl group, phenylalkenyl group, or phenylalkyl group wherein alkyl is $C_1$ to $C_7$ alkyl and alkenyl is $C_2$ to $C_7$ alkenyl, (c) a $C_1$ to $C_{18}$ alkyl or $C_2$ to $C_7$ alkenyl group which may be substituted by one or two substituents selected from $C_1$ to $C_5$ alkyl groups and quanidino groups, wherein an alkyl substituent together with the carbon atom to which it is attached may form a cycloalkyl ring having from 3 to 6 carbon atoms, or said $C_1$ to $C_5$ alkyl may itself be substituted by a $C_3$ to $C_6$ cycloalkyl ring, or (d) $-(CH_2)_n-NH-CO-(CH_2)_{n'}$ wherein n and n' may be the same or different and represent an integer from 1 to 4; and
wherein R denotes (e) a hydroxyl group, (f) a $C_1$ to $C_7$ alkoxy group which may be mono- or disubstituted by $C_1$ to $C_5$ alkyl, (g) a phenyl-$C_1$-$C_4$alkoxy group, (h) $-OAl(OH)_2$, (i) an amino group, (j)

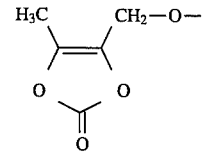

or (k)

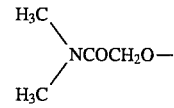

and pharmaceutically acceptable acid addition salts thereof, useful as pharmaceuticals.

44 Claims, No Drawings

AMIDINONAPHTHYL FURANCARBOXYLATE DERIVATIVES AND ACID ADDITION SALTS THEROF

REFERENCE TO A RELATED APPLICATION

This is a continuation-in-part of application Ser. No. 07/956,287, filed on Oct. 5, 1992, now abandoned, which is relied on and incorporated herein by reference in its entirety.

INTRODUCTION AND BACKGROUND

The present invention relates to novel amidinonaphthyl furancarboxylate derivatives and acid addition salts thereof, and pharmaceutical compositions containing them (either alone or in combination with at least one pharmaceutically acceptable carrier). The present invention also concerns methods of treating nephritis, methods of treating auto-immune diseases, methods of treating arthritis, and a method of at least partially inhibiting the in vitro activity of trypsin, plasmin, thrombin, kallikrein and/or complement in biological samples.

Various autoimmune diseases are known, including, for example, systemic lupus erythematosus, articular rheumatism, scleroderma, etc. Pharmaceuticals generally known at present for treating these diseases are steroidal agents. Steroidal agents are very difficult to use properly; for example, erroneous use of steroidal agents causes various side effects due to the lowering of immunological functions or the atrophy of the adrenal gland, and sometimes ultimately causes death.

It is generally said that nephritis and autoimmune diseases are closely related with proteases and complement.

Amidinonaphthyl furancarboxylate derivatives are known to have activities of inhibiting enzymes such as trypsin, plasmin, kallikrein, thrombin, etc., and of inhibiting complement. It has been suggested that these enzyme inhibitors are useful as agents for the treatment of pancreatitis, agents for the treatment of hemorrhagic diseases, agents for the treatment of thrombosis or agents for the treatment of nephritis (Japanese Patent Kokai (Laid-open) Nos. 59-139357 and 61-22075).

However, though these compounds all show strong anti-enzyme activities, they are not yet satisfactory in their effectiveness and safety.

SUMMARY OF THE INVENTION

An object of the present invention is to provide compounds which strongly inhibit the activity of trypsin, plasmin, thrombin, kallikrein or complement, exert no strong side effect unlike steroidal agents, and exhibit a stronger efficacy in treating nephritis and autoimmune diseases than the known compounds mentioned above.

Such compounds are amidinonaphthyl furancarboxylate derivatives of the formula I

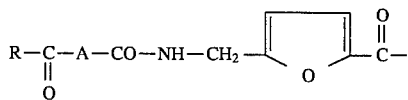

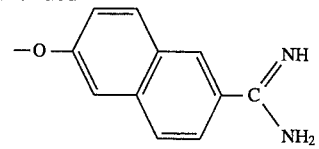

wherein A is a single bond or A denotes
(a) a phenyl group, cyclopentyl group, or cyclohexyl group,
(b) an alkenylphenyl group, alkylphenyl group, phenylalkenyl group, or phenylalkyl group wherein alkyl is $C_1$ to $C_7$ alkyl and alkenyl is $C_2$ to $C_7$ alkenyl,
(c) a $C_1$ to $C_{18}$ alkyl or $C_2$ to $C_7$ alkenyl group which may be substituted by one or two substituents selected from $C_1$ to $C_5$ alkyl groups and quanidino groups, wherein an alkyl substituent together with the carbon atom to which it is attached may form a cycloalkyl ring having from 3 to 6 carbon atoms, or said $C_1$ to $C_5$ alkyl may itself be substituted by a $C_3$ to $C_6$ cycloalkyl ring, or
(d) $-(CH_2)_n-NH-CO-(CH_2)_{n'}$ wherein n and n' may be the same or different and represent an integer from 1 to 4; and
wherein R denotes
(e) a hydroxyl group,
(f) a $C_1$ to $C_7$ alkoxy group which may be mono- or disubstituted by $C_1$ to $C_5$ alkyl,
(g) a phenyl-$C_1$-$C_4$alkoxy group,
(h) $-OAl(OH)_2$,
(i) an amino group,
(j)

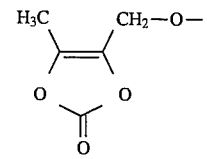

or
(k)

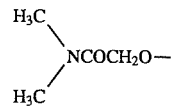

or pharmaceutically acceptable addition salts thereof.

Another object is to provdide a pharmaceutical preparation containing the above described derivative or the acid addition salt thereof in combination with at least one pharmaceutically acceptable carrier.

Another object of the present invention is to provide a method of treating nephritis involving administering to a mammal in need thereof an effective amount of the pharmaceutical composition described above.

An additional object of the present invention is to provide a method of treating auto-immune diseases involving administering to a mammal in need thereof an effective amount of the pharmaceutical composition described above.

Another object of the present invention is to provide a method of treating arthritis involving administering to a mammal in need thereof an effective amount of the pharmaceutical composition described above.

Another object of the present invention is to provide a method of at least partially inhibiting the in vitro activity of trypsin, plasmin, thrombin, kallikrein and/or complement involving adding to a sample an effective amount of the amidinonaphthyl furancarboxylate derivative described above.

DETAILED DESCRIPTION OF THE INVENTION

The compounds disclosed in Japanese Patent Kokai (Laid-open) Nos. 59-139357 and 61-22075 all contain neither carboxylic acid group nor its derivative at the terminal opposite to the amidinonaphthol group.

The present inventors converted the terminal portion of such compounds opposite to the amidinonaphthol group into a carboxylic acid or its derivative. Thus, this invention relates to amidinonaphthyl furancarboxylate derivatives of the formula I $$R-\underset{\underset{O}{\|}}{C}-A-CO-NH-CH_2-\underbrace{\phantom{xxx}}_{O}-\underset{\underset{}{\|}}{C}-$$

$$-O-\text{[naphthyl]}-\underset{NH_2}{\overset{NH}{\underset{\|}{C}}}$$ I wherein A is a single bond or A denotes (a) a phenyl group, cyclopentyl group, or cyclohexyl group, (b) an alkenylphenyl group, alkylphenyl group, phenylalkenyl group, or phenylalkyl group wherein alkyl is $C_1$ to $C_7$ alkyl and alkenyl is $C_2$ to $C_7$ alkenyl, (c) a $C_1$ to $C_{18}$ alkyl or $C_2$ to $C_7$ alkenyl group which may be substituted by one or two substituents selected from $C_1$ to $C_5$ alkyl groups and quanidino groups, wherein an alkyl substituent together with the carbon atom to which it is attached may form a cycloalkyl ring having from 3 to 6 carbon atoms, or said $C_1$ to $C_5$ alkyl may itself be substituted by a $C_3$ to $C_6$ cycloalkyl ring, or (d) $-(CH_2)_n-NH-CO-(CH_2)_{n'}-$ wherein n and n' may be the same or different and represent an integer from 1 to 4; and wherein R denotes (e) a hydroxyl group, (f) a $C_1$ to $C_7$ alkoxy group which may be mono- or disubstituted by $C_1$ to $C_5$ alkyl, (g) a phenyl-$C_1$-$C_4$alkoxy group, (h) $-OAl(OH)_2$, (i) an amino group, (j)

$$\underset{O}{\overset{H_3C}{\diagdown}}\underset{\underset{\|}{O}}{\underset{O}{\diagup}}\overset{CH_2-O-}{\diagup}$$

or (k)

$$\underset{H_3C}{\overset{H_3C}{\diagdown}}N-COCH_2O-$$

or pharmaceutically acceptable acid addition salts thereof.

The compounds of the present invention surprisingly strongly inhibit the activity of trypsin, plasmin, thrombin, kallikrein or complement. These compounds having protease inhibitory activities can be used, for example, as a stabilizer for preventing the decomposition of collected bloods due to these enzymatic activities, in the determination of fibrinopeptide etc. relating to the blood coagulation system. Thus, the amidinonaphthyl furancarboxylate derivatives described herein can stabilize blood collected for medical tests. As noted above, the present invention also concerns a method of at least partially inhibiting the in vitro activity of trypsin, plasmin, thrombin, kallikrein and/or complement involving adding to a sample (e.g., blood or plasma) an effective amount of the amidinonaphthyl furancarboxylate derivative described above. An effective amount would be easily determined by a person skilled in the art; the effective amount would be that amount which would inhibit the activity of trypsin, plasmin, thrombin, kallikrein or complement.

EXAMPLES

Anti-trypsin, Anti-plasmin, Anti-kallikrein and Anti-thrombin Activities

Table 1 shows the inhibitory activities of representative compounds of the present invention against trypsin, plasmin, complement, kallikrein and thrombin. The values in Table 1 represent molar concentrations ($IC_{50}$) of test compounds which inhibit 50% of the activity of each enzyme to hydrolyze TAME (tosylarginine methyl ester). The anti-trypsin, anti-plasmin, anti-kallikrein and anti-thrombin activities were determined according to the method of Muramatsu et al. (J. Biochem. (1965), volume 58, page 214).

Anti-complement Activity

The anti-C1 esterase ($C\bar{1}r$, $C\bar{1}s$) activity was determined according to the method of Okamura et al. (Biochem. Biophys. Acta (1973), volume 295, pages 252–257). The values for $C\bar{1}r$ in the Table I represent molar concentrations ($IC_{50}$) of test compounds which inhibit 50% of the activity of $C\bar{1}r$ to hydrolyze AAME (acetyl-arginine methyl ester). The values for $C\bar{1}s$ represent molar concentrations (IC50) of test compounds which inhibit 50% of the activity of $C\bar{1}s$ to hydrolyze ATEE (acetyltyrosine ethyl ester).

Table 1 shows the anti-trypsin, anti-plasmin, anti-kallikrein, anti-thrombin and anti-complement activities of representative compounds of the present invention.

TABLE 1

| Example No. | Try | Pla | $C\bar{1}r$ | $C\bar{1}s$ | Kal | Thr |
|---|---|---|---|---|---|---|
| 1 | $3.5 \times 10^{-7}$ | $1.5 \times 10^{-7}$ | $3.4 \times 10^{-7}$ | $2.7 \times 10^{-7}$ | $4.7 \times 10^{-7}$ | $3.5 \times 10^{-7}$ |
| 2 | $8.4 \times 10^{-6}$ | $4.8 \times 10^{-6}$ | $29(10^{-5})$ | $17(10^{-5})$ | $46(10^{-5})$ | $47(10^{-5})$ |

TABLE 1-continued

| Example No. | Try | Pla | ClF | ClS | Kal | Thr |
|---|---|---|---|---|---|---|
| 3 | 48($10^{-5}$)* | $8.6 \times 10^{-6}$ | 34($10^{-5}$) | $3.4 \times 10^{-6}$ | 33($10^{-5}$) | 26($10^{-5}$) |
| 4 | $3.4 \times 10^{-7}$ | $7.2 \times 10^{-8}$ | $6.4 \times 10^{-8}$ | $1.6 \times 10^{-7}$ | $2.1 \times 10^{-7}$ | $7.0 \times 10^{-8}$ |
| 5 | $3.4 \times 10^{-7}$ | $1.0 \times 10^{-7}$ | $7.3 \times 10^{-8}$ | $3.6 \times 10^{-7}$ | $3.0 \times 10^{-7}$ | $1.8 \times 10^{-7}$ |
| 6 | $3.9 \times 10^{-7}$ | $2.6 \times 10^{-7}$ | $2.3 \times 10^{-8}$ | $2.7 \times 10^{-7}$ | $8.3 \times 10^{-7}$ | $1.0 \times 10^{-5}$ |
| 7 | $1.8 \times 10^{-6}$ | $3.0 \times 10^{-7}$ | $7.4 \times 10^{-7}$ | $4.6 \times 10^{-7}$ | $1.5 \times 10^{-6}$ | $4.0 \times 10^{-7}$ |
| 8 | $2.1 \times 10^{-6}$ | $1.1 \times 10^{-6}$ | $8.3 \times 10^{-7}$ | $2.0 \times 10^{-6}$ | $2.7 \times 10^{-6}$ | $1.4 \times 10^{-6}$ |
| 9 | $4.8 \times 10^{-6}$ | $5.0 \times 10^{-7}$ | $2.8 \times 10^{-6}$ | $2.3 \times 10^{-6}$ | $6.0 \times 10^{-6}$ | $6.5 \times 10^{-7}$ |
| 10 | $6.0 \times 10^{-7}$ | $1.5 \times 10^{-7}$ | $1.6 \times 10^{-7}$ | $2.6 \times 10^{-8}$ | $2.5 \times 10^{-7}$ | $1.6 \times 10^{-6}$ |
| 11 | $6.6 \times 10^{-7}$ | $4.0 \times 10^{-7}$ | $1.2 \times 10^{-6}$ | $2.8 \times 10^{-7}$ | $8.7 \times 10^{-7}$ | $1.2 \times 10^{-6}$ |
| 12 | $4.8 \times 10^{-7}$ | $2.7 \times 10^{-7}$ | $2.8 \times 10^{-6}$ | $2.1 \times 10^{-7}$ | $7.7 \times 10^{-7}$ | $6.0 \times 10^{-7}$ |
| 15 | $7.1 \times 10^{-7}$ | $3.1 \times 10^{-7}$ | $8.4 \times 10^{-7}$ | $2.3 \times 10^{-7}$ | $3.2 \times 10^{-7}$ | $4.0 \times 10^{-7}$ |
| 16 | $3.4 \times 10^{-7}$ | $2.4 \times 10^{-7}$ | $6.9 \times 10^{-6}$ | $3.5 \times 10^{-7}$ | $3.8 \times 10^{-6}$ | $1.3 \times 10^{-6}$ |
| 17 | $4.7 \times 10^{-7}$ | $4.3 \times 10^{-8}$ | $1.7 \times 10^{-6}$ | $5.3 \times 10^{-8}$ | $1.1 \times 10^{-6}$ | $1.9 \times 10^{-6}$ |
| 18 | $4.0 \times 10^{-7}$ | $1.9 \times 10^{-7}$ | $3.4 \times 10^{-7}$ | $1.9 \times 10^{-7}$ | $2.1 \times 10^{-7}$ | $3.5 \times 10^{-7}$ |
| 19 | $2.5 \times 10^{-7}$ | $1.7 \times 10^{-7}$ | $1.8 \times 10^{-6}$ | $7.2 \times 10^{-7}$ | $2.5 \times 10^{-7}$ | $3.6 \times 10^{-7}$ |
| 20 | $2.0 \times 10^{-6}$ | $1.8 \times 10^{-7}$ | $3.8 \times 10^{-7}$ | $3.9 \times 10^{-7}$ | $1.3 \times 10^{-7}$ | $4.6 \times 10^{-7}$ |
| 21 | $3.1 \times 10^{-7}$ | $3.3 \times 10^{-7}$ | $5.4 \times 10^{-7}$ | $1.8 \times 10^{-7}$ | $7.0 \times 10^{-7}$ | $9.6 \times 10^{-7}$ |
| 22 | $4.3 \times 10^{-7}$ | $4.3 \times 10^{-7}$ | 49($10^{-5}$) | $2.5 \times 10^{-7}$ | $4.7 \times 10^{-7}$ | $3.5 \times 10^{-6}$ |
| 27 | $3.1 \times 10^{-7}$ | $3.3 \times 10^{-7}$ | $5.4 \times 10^{-7}$ | $1.8 \times 10^{-7}$ | $7.0 \times 10^{-7}$ | $9.6 \times 10^{-7}$ |
| 29 | $1.2 \times 10^{-6}$ | $2.3 \times 10^{-7}$ | $4.4 \times 10^{-7}$ | $3.6 \times 10^{-7}$ | $2.4 \times 10^{-7}$ | $1.6 \times 10^{-6}$ |
| 31 | $6.0 \times 10^{-7}$ | $1.6 \times 10^{-7}$ | $2.9 \times 10^{-7}$ | $4.5 \times 10^{-7}$ | $1.7 \times 10^{-7}$ | $1.5 \times 10^{-7}$ |
| 33 | $6.6 \times 10^{-6}$ | $8.4 \times 10^{-8}$ | $1.4 \times 10^{-7}$ | $2.2 \times 10^{-7}$ | $5.8 \times 10^{-7}$ | $2.3 \times 10^{-8}$ |
| 34 | $2.7 \times 10^{-7}$ | $1.3 \times 10^{-7}$ | $3.3 \times 10^{-7}$ | $1.7 \times 10^{-7}$ | $1.3 \times 10^{-7}$ | $8.9 \times 10^{-8}$ |

Note:
*Indicated in terms of percentage inhibition at a concentration of $1 \times 10^{-5}$ M.

The compounds of the present invention can be administered by various methods conventionally used for pharmaceuticals, for example, in such forms of preparation as oral preparations, injections, suppositories, ointments, creams, etc. The dosage forms of the oral preparations may be, for example, tablets, capsules, troches, powders, pills, granules, solutions or suspensions. These dosage forms may contain various additives, for example, binders such as gum arabic, gelatin, sorbitol, tragacanth, poly(vinyl pyrrolidone), poly(vinyl alcohol), hydroxypropyl methyl cellulose, crystalline cellulose, sodium carboxymethyl cellulose, etc.; vehicles such as lactose, sucrose, mannitol, corn starch, calcium phosphate, sorbitol, crystalline cellulose, etc.; lubricants such as magnesium stearate, talc, polyethylene glycol, silica, etc.; and disintegrators such as potato starch, hydroxypropyl cellulose of low substitution degree, calcium carboxymethyl cellulose, sodium carboxymethyl starch, etc., each alone or in combinations. Soft capsules may also contain conventionally used vehicles, such as vegetable oils, polyethylene glycol, etc., oily suspending agents, liquid preparations and wetting agents such as surfactants.

The liquid preparations may be, for example, oily or aqueous suspensions, syrups, elixirs, and lyophilized products which can be redissolved with water or other additives immediately before use. These liquid preparations may contain suspending agents such as methyl cellulose, sodium carboxymethyl cellulose, hydroxypropyl cellulose, hydroxypropyl methyl cellulose, poly(vinyl pyrrolidone) poly(vinyl alcohol), tragachanth, gelatin, sodium alginate, etc.; emulsifiers such as lecithin, sorbitan, fatty acid esters, gum arabic, tragacanth, etc.; wetting agents such as polyoxyethylene sorbitan fatty acid esters, polyoxyethylene fatty acid esters, hydrogenated castor oil, sesame oil, soybean oil, propylene glycol, polyethylene glycol, ethyl alcohol, etc.; antiseptics such as methyl p-hydroxybenzoate, propyl p-hydroxybenzoate, sorbic acid, etc.; and sweetness such as simple syrups, sucrose, sorbitol, mannitol, etc.; each alone or in combinations.

The rectal preparations may be prepared by using oily bases such as cacao butter, Witepsol, triglyceride, etc., or water-soluble bases such as glycerol, glycerogelatin, Macrogol, etc.

When a compound of the present invention is administered to humans for the purpose of therapy, the dose should be properly adjusted depending on the seriousness of disease, the age and body weight of the patient, and other factors known to those skilled in the art. For example, when the compound is administered to humans for treating autoimmune diseases or nephritis or arthritis, it is usually administered at a dose of 1–400 mg/man/day (0.02–8 mg/kg), preferably 30–300 mg/man/day (0.06–6 mg/kg), and more preferably 100–300 mg/man/day (2–6 mg/kg), for example in the form of capsule or tablet, 1 to 4 times per day for one month.

As an experimental example of treating autoimmune diseases, description is given of an experiment on adjuvant arthritis, and as that of treating nephritis an experiment on Masugi's nephritis (experimental glomerulonephritis).

EXPERIMENTAL EXAMPLE 1

Effectiveness in treating adjuvant arthritis

Adjuvant arthritis is known as a representative model of autoimmune diseases and is a effective means of testing agents to treat human rheumatoid arthritis (Encyclopedia of Immunology, edited by I. M. Roitt, Academic Press, 1992; Otterness, I. G., et al., J. of Rheumatology (1991), volume 18, pages 505–511), The method of experiment was as follows. A 0.6% *Mycobacterium butyricum* liquid paraffin suspension, 0.1 ml/animal, was administered to a rat at a subcutaneous site of left hind-limb sole to induce adjuvant arthritis. The present compound was orally administered (in the form of a suspension in water) consecutively from 1 day before the induction to 13 days after the induction. The efficacy of the present compound on adjuvant arthritis was evaluated by examining the swelling accompanied by red spots and subcutaneous knots at the fore-limb, hind-limb, tail, ear and periphery of eye with the lapse of days (on the 8th, 10th, 12th, 14th, 16th and 18th days after adjuvant administration), expressing the results in terms of scores according to the method of F. D. Wood et al. (Int. Arch. Allergy (1969), volume 35, pages 456–467), and calculating the percentage inhibition relative to the control group. Thus, the higher value of percentage inhibition indicates the higher effectiveness. The results obtained are shown in Table 2.

TABLE 2

| Example No. | Dose (mg/kg) | Percentage*⁾ inhibition (%) |
|---|---|---|
| 31 | 30 | 67.7 |
| 17 | 60 | 75.1 |
| 22 | 60 | 97.3 |

Note
*⁾(Score of animal administered with present compound) ÷ (Score of untreated animal) × 100

EXPERIMENTAL EXAMPLE 2

Effectiveness in treating Masugi's nephritis (experimental glomerulonephritis)(Encyclopedia of Immunology, edited by I. M. Roitt, Academic Press, 1992; Nagai, H., et al., Int. J. Immunopharmac. (1983), volume 5, pages 235–244)

The present compound was orally administered (in a suspension in water) at a dose of 30 mg/kg. The control compounds used were known compounds I and II shown below selected as those having a relatively strong enzyme inhibitory activity from the compounds described in Japanese Patent Kokai (Laid-open) Nos. 59-139357 and 61-22075, which were orally administered respectively at a dose of 100 mg/kg and compared with the present compounds in effectiveness.

As the index to effectiveness, the protein concentration in urine was determined. That is, when inflammation develops in the kidney, it causes damage to renal tubules, etc., and a resultant increase in protein concentration in urine.

The results thus obtained are shown in Table 3. As is apparent from the Table, the administration of the present compounds distinctly and surprisingly reduces the protein concentration in urine as compared with non-administered group. Further, it is recognized that while the known compounds are effective at a dose of 100 mg/kg, the present compounds are unexpectedly effective at one third the dose.

TABLE 3

| Example No. | Dose (mg/kg) | Protein concentration in urine *1) (mg/ml) |
|---|---|---|
| Control group | 0 | 40.8 ± 15.1 |
| 6 | 30 | 19.7 ± 11.1 |
| 11 | 30 | 33.6 ± 17.8 |
| 13 | 30 | 24.2 ± 16.8 |
| 17 | 10 | 2.0 ± 2.0 |
| 22 | 30 | 3.0 ± 2.0 |
| 23 | 30 | 24.2 ± 18.8 |
| 26 | 30 | 25.0 ± 15.4 |
| 32 | 30 | 22.8 ± 13.9 |
| 34 | 30 | 29.3 ± 18.8 |
| 36 | 30 | 26.2 ± 14.7 |
| 38 | 30 | 17.8 ± 12.4 |
| 43 | 30 | 21.8 ± 10.3 |
| 44 | 30 | 20.0 ± 12.9 |
| Known compd. I *2) | 100 | 24.4 ± 11.9 |
| Known compd. II *3) | 100 | 22.1 ± 11.4 |

Note
*1) Expressed in terms of mean value ± standard deviation for 7 animals.
*2) Known compound I (Japanese Patent Kokai (Laid-open) No. 61-22075)

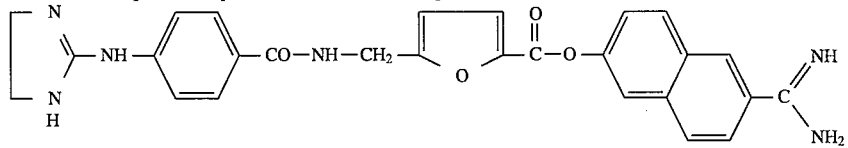

*3) Known compound II (Japanese Patent Kokai (Laid-open) No. 59-139357)

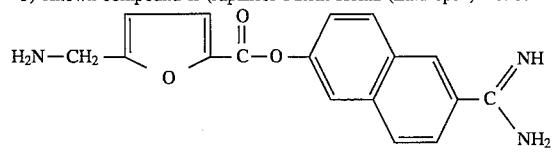

A kidney medulla antiserum of rat, 0.5 ml, obtained by immunizing a rabbit with a homogenate of kidney medulla of a rat together with Freund's complete adjuvant was administered to a rat through the tail vein to induce nephritis.

EXPERIMENTAL EXAMPLE 3

Effect of TO-195 on Masugi's nephritis and rabbit serum albumin (RSA) nephritis in rats.

4-{2-[5-(6-Amidino-2-naphthoxycarbonyl)furanyl]methyl carbamoyl}butyric acid (TO-195; the compound of Example 22 below) is an inhibitor of serine proteases including trypsin, thrombin, kallikrein, and C1r and C1s. Anti-nephritic effects of TO-195 were investigated in two animal models.

In Masugi's nephritis model, oral administration of TO-195 (in the form of a suspension in water, 6 mg/ml) at the dose of 3, 10, or 30 mg/kg×2/day from 2 days before through day 10 after nephrotoxin injection significantly decreased urinary protein excretion in rats. Light microscopic examination of the glomeruli revealed the significant anti-nephritic effect of TO-195 at 10 and 30 mg/kg×2/day compared to the control group.

Oral administration of TO-195 twice a day from day 4 to day 10 after injection of nephrotoxin also significantly decreased urinary protein excretion.

About 90% of human glomerular nephritis has been described as being immune complex nephritis which is caused by deposition in the glomeruli of immune complexes formed by the binding of antigens with antibodies in the blood. Effectiveness in treating rabbit serum albumin (RSA) nephritis in rats, which is known as an experimental model of nephritis caused by antigen-antibody reaction (Folia pharmacol. japon, 78: 491–499 (1981)), is shown below:

Sprague Dawley rats were immunized by subcutaneous injection in the back of 3 mg rabbit serum albumin in complete Freud's adjuvant (CFA). Two weeks after the subcutaneous injection, the rats were administered 1 mg of RSA (in saline) into the tail vein every other day for 10 weeks. Seven weeks after the first subcutaneous injection, the rats were also boosted with 3 mg RSA as in the first subcutaneous injection. The control group was injected with saline. Two weeks after the first IV injection, rats with more than 100 mg/day proteinurea after IV administration of RSA were divided into two groups each consisting of five rats. One group was orally given 30 mg/kg of TO-195 (in a suspension in water) twice a day for 20 days. The other group (untreated) and the control group were given distilled water p.o. (oral administration). The index of effectiveness of TO-195 was protein concentration in urine.

TABLE 4

|  | Protein concentration in urine (mg/ml)* |
| --- | --- |
| Treated | 152.1 ± 49.11 |
| Untreated | 385.9 ± 187.23 |
| Control | 8.5 ± 2.62 |

*Expressed in terms of mean value ± standard deviation for five animals

Thus, in rabbit serum albumin (RSA) nephritis in rats, oral administration of TO-195 at the dose of 30 mg/kg×2/day decreased urinary protein excretion; in addition, N-acetyl-β-D-glucosamineidase and alkaline phosphatase excretion were decreased.

Thus, the above results show that TO-195 can be used as an anti-nephritis drug.

EXPERIMENTAL EXAMPLE 4

Toxicity of a representative compound

The toxicity of the compound of Example 22 (described below) was determined as follows:

In the rat acute toxicity test, the $LD_{50}$ was greater than 2,000 mg/kg (p.o. oral administration). The compound of Example 22 was tested in three groups (five rats per group) of rats at dosages of (1) 2000 mg/kg, (2) 1000 mg/kg, and (3) 500 mg/kg; the compound was prepared in the form of a suspension in distilled water and administered orally. After the administration, general conditions and survival of the rats were observed for two weeks; no changes were found even in the group receiving 2,000 mg/kg.

In the monkey subacute toxicity test, no toxicity was recognized for three months after oral administration of the compound of Example 22, even at a dosage of 300 mg/kg. The compound of Example 22 was tested in three groups (five monkeys per group) of monkeys at dosages of (1) 3 mg/kg/day, (2) 30 mg/kg/day, and (3) 300 mg/kg/day; the compound was administered orally (dose volume was 2 ml/kg) by gavage once a day for 13 weeks. Administration was followed by 20 ml sterile water per animal. Control monkeys received only the vehicle (sterile water for injection, U.S.P.) on the same regimen as the experimental groups. All doses were administered using a 18 French rubber catheter attached to a syringe. After the administration, general conditions, biochemical examination, and survival were observed for 13 weeks; no changes were found even in the group receiving 300 mg/kg.

Toxicity in humans (Phase I study): This test was for confirmation of the safety of the drug (which was administered to healthy male adult volunteers). Taking into consideration the above toxicity tests, the compound of Example 22 was prepared in the form of capsules containing the compound in an increasing amount (from 5 mg/man to 400 mg/man (body weight 50–60 kg)). No adverse side effects were found even at the maximum dosage of 400 mg/man.

Some examples of pharmaceutical formulations according to this invention are shown below:

FORMULATION EXAMPLE 1

| The present compound | 50 mg |
| --- | --- |
| Lactose | 23 mg |
| Avicel | 50 mg |
| Carboxycellulose | 25 mg |
| Succinic acid | 50 mg |
| Magnesium stearate | 2 mg |

The total, 200 mg, is filled into a capsule or formed into a tablet.

FORMULATION EXAMPLE 2

| The present compound | 50 mg |
| --- | --- |
| Lactose | 68 mg |
| Avicel | 50 mg |
| Carboxycellulose | 30 mg |
| Magnesium stearate | 2 mg |

The total, 200 mg, is filled into a capsule or formed into a tablet.

FORMULATION EXAMPLE 3

| The present compound | 50 mg |
| --- | --- |
| Lactose | 27 mg |
| Corn starch | 27 mg |
| Hydroxypropyl starch | 15 mg |
| Magnesium stearate | 1 mg |

The total, 120 mg, is filled into a capsule or formed into a tablet.

FORMULATION EXAMPLE 4

| | |
|---|---|
| The present compound | 50 mg |
| Lactose | 27 mg |
| Corn starch | 27 mg |
| Hydroxypropyl cellulose of low substitution degree | 15 mg |
| Magnesium stearate | 1 mg |

The total, 120 mg, is filled into a capsule or formed into a tablet.

FORMULATION EXAMPLE 5

| | |
|---|---|
| The present compound | 50 mg |
| Hydroxypropyl starch | 37 mg |
| Hydroxypropyl cellulose of low substitution degree | 32 mg |
| Magnesium stearate | 1 mg |

The total, 120 mg, is filled into a capsule or formed into a tablet.

FORMULATION EXAMPLE 6

| | |
|---|---|
| The present compound | 50 mg |
| Lactose | 46.5 mg |
| Crystalline cellulose | 28 mg |
| Carboxymethyl cellulose | 18 mg |
| Polyvinylpyrrolidone K30 (av. MV 30,000) | 6 mg |
| Magnesium stearate | 1.5 mg |

The total, 150 mg, is filled into a capsule.

This invention is described in more detail below with reference to the Examples, but it is in no way limited thereto.

EXAMPLE 1

6-Amidino-2-naphthyl 5-[4-(2-t-butoxycarbonylvinyl)benzoylaminomethyl]furan-2-carboxylate hydrobromide In 15 ml of pyridine and 4 ml of N,N-dimethylacetamide (hereinafter abbreviated as DMA) were dissolved 2.0 g of 4-(2-t-butoxycarbonylvinyl)benzoic acid and 0.1 g of 4-dimethylaminopyridine (hereinafter abbreviated as DMAP) and the solution was stirred while cooling with ice. Then, 1.99 g of N,N'-dicyclohexylcarbodiimide (hereinafter abbreviated as DCC) was added to the mixture obtained above. The mixture was stirred at the same temperature for 30 minutes and then 3.49 g of 6-amidino-2-naphthyl 5-aminomethylfuran-2-carboxylate dihydrobromide was added thereto. The reaction mixture was stirred for 3 hours while cooling with ice and then overnight at room temperature, and the precipitated N,N'-dicyclohexylurea (hereinafter abbreviated as DCU) was separated by filtration and washed with a small amount of DMA. The filtrate was added dropwise to 800 ml of ether while stirring and cooling with ice. After the precipitate formed had sedimented, the supernatant was removed by decantation, then 400 ml of acetone was added to the residue and the mixture was stirred for 1 hour at room temperature. After repeating the procedure twice, the precipitated crystals were collected by filtration to obtain 1.88 g of the intended product.

IR$v_{max}^{KBr}$ cm$^{-1}$: (—COO—) 1720 NMR (DMSO-d$_6$) δppm: 9.86–8.84 (5H, br) 8.72–7.30 (12H, m) 6.67 (1H, d, J=3.5 Hz) 6.61 (1H, d, J=16.4 Hz) 4.64 (2H, d, J=4.4 Hz) 1.49 (9H, s)

EXAMPLE 2

6-Amidino-2-naphthyl 5-[4-(2-carboxyvinyl)benzoylaminomethyl]furan-2-carboxylate hydrochloride In 80 ml of acetic acid was dissolved 4 g of 6-amidino-2-naphthyl 5-[4-(2-t-butoxycarbonylvinyl)benzoylaminomethyl]furan-2-carboxylate hydrochloride. Then, hydrogen chloride gas was bubbled into the resulting solution for 1 hour while stirring and cooling with water. The precipitate was collected by filtration and washed with 120 ml of acetone to obtain 2.8 g of the intended product.

m.p.: 249°–252.6° C. IR$v_{max}^{KBr}$ cm$^{-1}$: (—COO—) 1705 NMR (DMSO-d$_6$) δppm: 12.12 (1H, br) 10.14–8.91 (5H, br) 8.75–7.30 (12H, m) 6.67 (1H, d, J=3.5 Hz) 6.65 (1H, d, J=16.1 Hz) 4.63 (2H, d, J=4.4 Hz)

EXAMPLE 3

6-Amidino-2-naphthyl 5-(4-carboxybenzoylaminomethyl)furan-2-carboxylate hydrochloride To 5 g of terephthalic acid, 3.83 g of 6-amidino-2-naphthyl 5-aminomethylfuran-2-carboxylate dihydrochloride and 0.12 g of DMAP were added 40 ml of N,N-dimethylformamide (hereinafter abbreviated as DMF) and 40 ml of pyridine, the mixture was stirred for 30 minutes while cooling with ice, and then 2.48 g of DCC was added thereto. The mixture was stirred for 1 hour while cooling with ice and for 4 hours while cooling with water. The precipitate was separated by filtration and washed with 5 ml of DMF. The filtrate was added in small portions to 600 ml of ether and the mixture was stirred for 30 minutes at room temperature. Thereafter, the supernatant was removed by decantation and the residue was washed 3 times with 300 ml of acetone with stirring at room temperature.

The crude crystals were dissolved in 36 ml of DMF, then 80 ml of acetone was added to the solution while cooling with water and stirring, and the mixture was stirred for 1 hour. The precipitate was collected by filtration and washed with acetone to obtain 2.2 g of the intended product.

m.p.: 247°–248.5° C. IR$v_{max}^{KBr}$ cm$^{-1}$: (—COO—) 1720

In the same manner as in Example 1 but by using appropriate starting materials, the respective compounds of the following Examples 4 and 5 were obtained.

EXAMPLE 4

6-Amidino-2-naphthyl 5-(4-methoxycarbonylmethylbenzoylaminomethyl)furan-2-carboxylate hydrochloride.

m.p.: 216°–218° C. IR$v_{max}^{KBr}$ cm$^{-1}$: (—COO—) 1730 NMR (DMSO-d$_6$) δppm: 10.02–8.90 (5H, m) 8.81–7.09 (11H, m) 6.64 (1H, d, J=3.5 Hz) 4.61 (2H, d, J=5.6 Hz) 3.77 (2H, s) 3.63 (3H, s)

EXAMPLE 5

6-Amidino-2-naphthyl 5-(4-t-butoxycarbonylphenylacetylaminomethyl)furan-2-carboxylate hydrochloride.

m.p.: 178°–180.5° C. IR$\nu_{max}^{KBr}$ cm$^{-1}$: (—COO—) 1730, 1705 NMR (DMSO-d$_6$) δppm: 10.03–6.98 (16H, m) 6.56 (1H, d, J=3.2 Hz) 4.42 (2H, d, J=5.3 Hz) 3.61 (2H, s) 1.52 (9H, s)

EXAMPLE 6

6-Amidino-2-naphthyl 5-(4-carboxyphenylacetylaminomethyl)furan-2-carboxylate hydrochloride To 5.4 g of 6-amidino-2-naphthyl 5-(4-t-butoxycarbonylphenylacetylaminomethyl)furan-2-carboxylate hydrochloride was added 8 ml of acetic acid, and hydrogen chloride gas was passed into the mixture for 2 hours while stirring and cooling with ice. The mixture was further stirred for 2.5 hours with water-cooling, the precipitate was collected by filtration and washed twice with 20 ml of acetone. The crystals were dissolved in 20 ml of DMF, then 1 g of active carbon was added to the solution and stirred for 30 minutes while cooling with ice. The insolubles were removed by filtration, the filtrate was added to 250 ml of acetone and stirred for 2 hours at room temperature. The precipitate was collected by filtration to obtain 3.2 g of the intended product.

m.p.: 232°–235° C. IR$\nu_{max}^{KBr}$ cm$^{-1}$: (—COO—) 1720 NMR (DMSO-d$_6$) δppm: 13.88–11.95 (1H, br) 10.37–7.17 (16H, m) 6.57 (1H, d, J=3.5 Hz) 4.44 (2H, d, J=5.0 Hz) 3.64 (2H, s)

EXAMPLE 7

6-Amidino-2-naphthyl 5-(4-carboxymethylbenzoylaminomethyl)furan-2-carboxylate hydrochloride To 3 g of 6-amidino-2-naphthyl 5-(4-methoxycarbonylmethylbenzoylaminomethyl)furan-2-carboxylate hydrochloride was added 60 ml of acetic acid, and hydrogen chloride gas was passed into the mixture until saturation while cooling with ice and stirring. Thereafter the mixture was stirred for 48 hours at 50° C. and then cooled with ice. The precipitate was collected by filtration and washed with 100 ml of acetone. The crystals were dissolved in 40 ml of DMF, then 1 g of active carbon was added to the solution and stirred for 1 hour while cooling with ice. Thereafter, the insolubles were removed by filtration, 90 ml of acetone was added to the filtrate and stirred for 18 hours at room temperature. The precipitate was collected by filtration and washed with 50 ml of acetone to obtain 1.3 g of the intended product.

m.p.: 225°–228° C. IR$\nu_{max}^{KBr}$ cm$^{-1}$: (—COO—) 1730 NMR (DMSO-d$_6$) δppm: 12.41 (1H, br) 10.11–8.95 (5H, m) 8.77–7.13 (11H, m) 7.60 (1H, d, J=3.5 Hz) 6.65 (1H, d, J=3.2 Hz) 4.62 (2H, d, J=5.0 Hz) 3.94–3.51 (2H, m)

EXAMPLE 8

In the same manner as in Example 6 but by using an appropriate starting material, the following compound was obtained.

6-Amidino-2-naphthyl 5-(4-carboxycinnamoylaminomethyl)furan-2-carboxylate hydrochloride m.p.: 241°–245° C. IR$\nu_{max}^{KBr}$ cm$^{-1}$: (—COO—) 1720 NMR (DMSO-d$_6$) δppm: 13.07 (1H, br) 9.95–7.21 (17H, m) 7.15–6.43 (2H, m) 4.59 (2H, d, J=5.9 Hz)

EXAMPLE 9

6-Amidino-2-naphthyl 5-[4-(2-carboxyethyl)benzoylaminomethyl]furan-2-carboxylate hydrochloride To a solution of 1.1 g of 6-amidino-2-naphthyl 5-(2-carboxyvinyl)benzoylaminomethyl]furan-2 -carboxylate hydrochloride in 18 ml of DMF was added 180 mg of 10% palladium-carbon and the mixture was subjected to catalytic reduction at room temperature for 10 hours. The insolubles were removed by filtration and the filtrate was added dropwise to 300 ml of ether with stirring. The white solid thus precipitated was collected by filtration to obtain 990 mg of the intended product.

m.p.: 208°–210.5° C. IR$\nu_{max}^{KBr}$ cm$^{-1}$: (—COO—) 1720 NMR (DMSO-d$_6$) δppm: 12.13 (1H, brs) 10.03–8.90 (5H, m) 8.72–7.05 (11H, m) 6.63 (1H, d, J=3.5 Hz) 4.60 (2H, d, J=5.3 Hz) 3.15–2.28 (4H, m)

EXAMPLE 10

6-Amidino-2-naphthyl 5-(cis-4-carboxy-1-cyclohexanoylaminomethyl)furan-2-carboxylate hydrochloride The same procedures as in Example 3 were followed except for using 11.5 g of 6-amidino-2-naphthyl 5-aminomethylfuran-2-carboxylate dihydrochloride and 15.5 g of cis-1,4-cyclohexanedicarboxylic acid, to obtain 5.0 g of the above-mentioned compound in crude form. The crude compound was dissolved in 100 ml of aqueous 90% methanol, 2% aqueous sodium hydrogencarbonate solution was added thereto, and the precipitated carbonate was collected by filtration and washed with water. The washed product was made into solution by addition of 10 ml of DMF and 0.5 ml of hydrochloric acid, and the solution was added dropwise to 150 ml of acetone while stirring and cooling with ice. The white solid thus precipitated was collected by filtration to obtain 1.3 g of the intended product.

IR$\nu_{max}^{KBr}$ cm$^{-1}$: (—COO—) 1722 NMR (DMSO-d$_6$) δppm: 12.01 (1H, brs) 10.07–9.00 (4H, br) 8.80–7.25 (8H, m) 6.53 (1H, d, J=3.5 Hz) 4.38 (2H, d, J=5.0 Hz) 2.66–0.77 (10H, m)

EXAMPLE 11

6-Amidino-2-naphthyl 5-(trans-4-carboxy-1-cyclohexanoylaminomethyl)furan-2-carboxylate hydrochloride In the same manner as in Example 10 but by using an appropriate starting material, the above-mentioned compound was obtained.

m.p.: 242°–244° C. IR$\nu_{max}^{KBr}$ cm$^{-1}$: (—COO—) 1740 NMR (DMSO-d$_6$) δppm: 11.76 (2H, br) 10.10–9.03 (4H, br) 8.86–7.30 (8H, m) 6.54 (1H, d, J=3.5 Hz) 4.39 (2H, d, J=4.7 Hz) 2.69–0.79 (10H, m)

EXAMPLE 12

6-Amidino-2-naphthyl 5-(cis-2-carboxyvinyl)carbonylaminomethylfuran-2-carboxylate methanesulfonate In 240 ml of DMF was dissolved 7.7 g of 6-amidino-2-naphthyl 5-aminomethylfuran-2-carboxylate dihydrochloride, and 240 mg of DMAP and 160 ml of pyridine were added thereto. Then, 7 g of maleic acid and 8.2 g of DCC were added to the mixture while stirring and cooling with ice and allowed to react for 2 hours. The precipitate was removed by filtration, the filtrate was added dropwise to 3 l of ether with stirring, the supernatant was removed, then 500 ml of acetone was added to the residue and the resulting precipitate was collected by filtration. The collected precipitate was made into a solution by addition of 40 ml of DMF and 2.0 g of methanesulfonic acid, and the solution was added dropwise to 800 ml of ether with stirring and water-cooling. The supernatant was removed, 50 ml of acetone was added to the residue, then stirred, 800 ml of ether was further added, and the resulting mixture was stirred. The white precipitate was collected by filtration to obtain 2.3 g of the intended product.

IR$v_{max}^{KBr}$ cm$^{-1}$: (—COO—) 1710 NMR (DMSO-d$_6$) δppm: 10.05–8.86 (5H, m) 8.76–7.42 (7H, m) 6.71 (1H, d, J=3.5 Hz) 6.49 (1H, d, J=12.3 Hz) 6.24 (1H, d, J=12.2 Hz) 4.54 (2H, d, J=5.3 Hz) 2.47 (3H, s)

EXAMPLE 13

6-Amidino-2-naphthyl 5-(trans-2-carboxyvinyl)carbonylaminomethylfuran-2-carboxylate hydrochloride In the same manner as in Example 12 but by using an appropriate starting material, the above-mentioned compound was obtained.

IR$v_{max}^{KBr}$ cm$^{-1}$: (—COO—) 1730, 1715, 1702 NMR (DMSO-d$_6$) δppm: 10.16–8.97 (8H, m) 8.81–6.29 (10H, m) 7.03 (1H, d, J=15.5 Hz) 6.67 (1H, d, J=4.4 Hz) 6.57 (1H, d, J=15.5 Hz) 4.54 (2H, d, J=5.6 HZ)

EXAMPLE 14

6-Amidino-2-naphthyl 5-t-butoxyoxalylaminomethylfuran-2-carboxylate hydrochloride In a mixture of 160 ml of pyridine and 240 ml of DMF were dissolved 6.5 g of mono-t-butyl oxalate, 7.7 g of 6-amidino-2-naphthyl 5-aminomethylfuran-2-carboxylate dihydrochloride and 250 mg of DMAP, then 8.3 g of DCC was added thereto with stirring and ice-cooling and the mixture was stirred for 24 hours. The precipitate was removed by filtration, the filtrate was added dropwise to 3 l of ether with stirring, the precipitated oily substance was dissolved in a small amount of methanol, and the resulting solution was added dropwise to 2 l of ether with stirring. The precipitate was collected by filtration to obtain 9.0 g of the intended product as a white solid.

IR$v_{max}^{KBr}$ cm$^{-1}$: (—COO—) 1730 NMR (DMSO-d$_6$) δppm: 10.14–9.08 (5H, m) 9.07–6.85 (7H, m) 6.65 (1H, d, J=3.2 Hz) 4.47 (2H, d, J=5.9 Hz) 1.50 (9H, s)

EXAMPLE 15

6-Amidino-2-naphthyl 5-t-butoxymalonylaminomethylfuran-2-carboxylate hydrochloride In the same manner as in Example 14 but by using an appropriate starting material, the above-mentioned compound was obtained.

IR$v_{max}^{KBr}$ cm$^{-1}$: (—COO—) 1730, 1720 NMR (DMSO-d$_6$) δppm: 10.68–9.13 (4H, br) 9.07–7.24 (8H, m) 6.63 (1H, d, J=3.2 Hz) 4.43 (2H, d, J=5.3 Hz) 3.23 (2H, s) 1.41 (9H, s)

EXAMPLE 16

6-Amidino-2-naphthyl 5-oxaloaminomethylfuran-2-carboxylate hydrochloride

In 50 ml of acetic acid was dissolved 7.0 g of 6-amidino-2-naphthyl 5-t-butoxyoxalylaminomethylfuran-2-carboxylate hydrochloride, and hydrogen chloride gas was bubbled into the solution with stirring and water-cooling for 20 minutes. The precipitate was collected by filtration and washed with acetone to obtain 2.7 g of the intended product as a white solid.

m.p.: 210.6°–215.9° C. IR$v_{max}^{KBr}$ cm$^{-1}$: (—COO—) 1720 NMR (DMSO-d$_6$) δppm: 10.30–9.03 (5H, m) 9.00–6.97 (8H, m) 6.64 (1H, d, J=3.5 Hz) 4.49 (2H, d, J=5.5 Hz)

EXAMPLE 17

6-Amidino-2-naphthyl 5-carboxyacetylaminomethylfuran-2-carboxylate hydrochloride To a mixture of 210 ml of DMF and 90 ml of pyridine were added 10 g of 6-amidino-2-naphthyl 5-aminomethylfuran-2-carboxylate dihydrochloride, 13.6 g of malonic acid and 320 mg of DMAP, then 10.8 g of DCC was added to the mixture with stirring and ice-cooling, and the mixture was stirred for 24 hours. The precipitate was removed by filtration and the filtrate was added dropwise to 3 l of acetone. The precipitate was collected by filtration to obtain 6.5 g of the intended product as a white solid.

IR$v_{max}^{KBr}$ cm$^{-1}$: (—COO—) 1718 NMR (DMSO-d$_6$) δppm: 10.58–9.17 (4H, br) 9.17–7.17 (8H, m) 6.65 (1H, d, J=3.5 Hz) 4.46 (2H, d, J=5.9 Hz) 3.63–2.98 (2H, m)

EXAMPLE 18

6-amidino-2-naphthyl 5-(3-t-butoxycarbonylpropionylaminomethyl)furan-2-carboxylate hydrochloride.

To 11.4 g of mono-t-butyl succinate, 23.5 g of 6-amidino-2-naphthyl 5-aminomethylfuran-2-carboxylate dihydrochloride and 0.66 g of DMAP was added 115 ml of pyridine, and the mixture was stirred with ice-cooling. After 10 minutes, 25.6 g of DCC was added and the mixture was stirred for 3 hours while cooling with ice and for 16 hours at room temperature. The precipitated crystals were filtered off, and the filtrate was added in small portions into 2 l of ether and stirred at room temperature for 3 l hours. After removing the supernatant by decantation, 1 l of acetone was added to the residue and stirred for 1 hour. The precipitate was collected by filtration, then dissolved in 60 ml of methanol and 3 g of active carbon was added to the solution. The mixture was stirred for 30 minutes while cooling with ice, then the insolubles were filtered off and the filtrate was added into 1.5 l of acetone. The mixture was stirred for 5 hours while cooling with ice, and the precipitated crystals were collected by filtration to obtain 21 g of the intended product.

IR$v_{max}^{KBr}$ cm$^{-1}$: (—COO—) 1720 NMR (DMSO-d$_6$) δppm: 9.43 (4H, br) 8.88–7.07 (8H, m) 6.59 (1H, d, J=3.5 Hz) 4.40 (2H, d, J=5.3 Hz) 2.42 (4H, s) 1.38 (9H, s)

EXAMPLE 19

In the same manner as in Example 18 but by using an appropriate starting material, the following compound was obtained.

6-Amidino-2-naphthyl 5-(4-t-butoxycarbonyl-butyrylaminomethyl)furan-2-carboxylate hydrochloride m.p.: 158.2°–161.8 °C. IR$v_{max}^{KBr}$ cm$^{-1}$: (—COO—) 1730, 1715 NMR (DMSO-d$_6$) δppm: 10.07–9.12 (4H, br) 8.98–7.27 (8H, m) 6.58 (1H, d, J=3.5 Hz) 4.40 (2H, d, J=5.9 Hz) 2.84–0.76 (15H, m)

EXAMPLE 20

6-amidino-2-naphthyl 5-(4-t-butoxycarbonyl-2-guanidinobutyrylaminomethyl)furan-2-carboxylate hydrochloride hydrobromide To 4.6 g of 4-t-butoxycarbonyl-2-guanidinobutyric acid hydrochloride, 5.3 g of 6-amidino-2-naphthyl 5-aminomethylfuran-2-carboxylate dihydrobromide and 220 mg of DMAP were added 110 ml of DMA and 36 ml of pyridine and the resulting mixture was stirred while cooling with ice. After 10 minutes, 4 g of DCC was added and the mixture was stirred for 3 hours while cooling with ice and then for 16 hours at room temperature. The precipitated were filtered off, the filtrate was added in small portions into 3 l of ether and stirred at room temperature for 3 hours. After removing the supernatant by decantation, the residue was dissolved in 60 ml of DMF, then 3 g of active carbon was added thereto, and the mixture was stirred for 30 minutes while cooling with ice. The insolubles were filtered off, and the filtrate was added dropwise into 3 l of ether and stirred for 5 hours while cooling with ice. The crystals thus precipitated were collected by filtration to obtain 6.7 g of the intended product.

IR$v_{max}^{KBr}$ cm$^{-1}$: (—COO—) 1720 NMR (DMSO-d$_6$) δppm: 9.80–6.86 (7H, m) 6.63 (1H, d, J=3.8 Hz) 4.74–4.04 (3H, m) 2.57–1.84 (4H, m) 1.38 (9H, s)

EXAMPLE 21

6-amidino-2-naphthyl 5-(3-carboxypropionylaminomethyl)furan-2-carboxylate hydrochloride To 22.3 g of succinic acid, 24.0 g of 6-amidino-2-naphthyl 5-aminomethylfuran-2-carboxylate dihydrochloride and 790 mg of DMAP was added 240 ml of pyridine, and the mixture was stirred while cooling with ice. After 10 minutes, 25.9 g of DCC was added and the mixture was stirred for 3 hours while cooling with ice and then for 16 hours at room temperature. The precipitate was filtered off, and the filtrate was added in small portions into 2 l of ether and stirred at room temperature for 3 hours. After removing the supernatant by decantation, 1 l of acetone was added to the residue and stirred for 3 hours. The precipitate was collected by filtration to obtain 24.0 g of the intended product.

m.p.: 218°–219.8° C. IR$v_{max}^{KBr}$ cm$^{-1}$: (—COO—) 1722 NMR (DMSO-d$_6$) δppm: 12.14 (1H, br) 10.17–9.10 (4H, br) 8.92–7.37 (8H, m) 6.59 (1H, d, J=3.5 Hz) 4.40 (2H, d, J=5.9 Hz) 2.46 (4H, s)

EXAMPLE 22

6-Amidino-2-naphthyl 5-(4-carboxybutyrylaminomethyl)furan-2-carboxylate hydrochloride Preparation Method 1

To 11.3 g of glutaric acid and 6.5 g of 6-amidino-2-naphthyl 5-aminomethylfuran-2-carboxylate dihydrochloride was added 50 ml of pyridine and the resulting mixture was stirred while cooling with ice. After 10 minutes, 4.3 g of DCC was added and the mixture was stirred for 3 hours while cooling with ice and then for 16 hours at room temperature. The precipitate was collected by filtration and washed with acetone. Then, 50 ml of DMF and 10 ml of saturated solution of hydrogen chloride in acetic acid were added to the crystals while cooling with water and stirred for 1 hour. The insolubles were removed by filtration, 3.5 g of active carbon was added to the filtrate and the resulting mixture was stirred for 30 minutes. The insolubles were filtered off and the filtrate was added dropwise into 300 ml of ether and stirred for 5 hours while cooling with ice. The supernatant was decanted, and 300 ml of acetone was added to the residue and stirred for 16 hours. The precipitate formed was collected by filtration and washed with 300 ml of acetone to obtain 3.0 g of the intended product.

m.p.: 189°–193° C. IR$v_{max}^{KBr}$ cm$^{-1}$: (—COO—) 1708 NMR (DMSO-d$_6$) δppm: 10.21–8.98 (4H, br) 8.86–7.32 (8H, m) 6.58 (1H, d, J=3.5 Hz) 4.40 (2H, d, J=6.5 Hz) 2.74–1.32 (6H, m)

Preparation Method 2

The intended compound can be synthesized in the same manner as in Example 6 by using the compound of Example 19.

Preparation Method 3

To 8 g of 6-amidino-2-naphthyl 5-aminomethyl-furan-2-carboxylate dihydrochloride, 3.6 g of glutaric anhydride and 1.72 g of anhydrous sodium acetate was added 50 ml of DMF, and the resulting mixture was stirred at 20° C. for 20 hours.

The insolubles thus precipitated were filtered off, 0.8 g of active carbon was added to the filtrate and the mixture was stirred for 2 hours while cooling with ice. The active carbon was filtered off, the filtrate was slowly added into 900 ml of acetone with stirring and ice-cooling, and stirred at the same temperature for 5 hours.

The precipitate was collected by filtration, then added to 450 ml of water, and the mixture was stirred for 4 hours at 70° C. and then overnight with ice-cooling.

The crystals were collected by filtration, then added to a mixture of 80 ml of DMF and 16 ml of acetic acid containing 8% of hydrogen chloride gas, 0.8 g of active carbon was added thereto, and the mixture was stirred for 2 hours while cooling with ice. The insolubles were filtered off, the filtrate was added into 800 ml of acetone while stirring and cooling with ice, and the mixture was stirred at the same temperature for 5 hours.

The crystals thus precipitated were collected by filtration and washed with 80 ml of acetone to obtain 7.6 g of the intended product.

In the same manner as in Example 21 but by using appropriate starting materials, the compounds of Example 23 to 26 shown below were obtained.

EXAMPLE 23

6-Amidino-2-naphthyl 5-(5-carboxyvalerylaminomethyl)furan-2-carboxylate hydrochloride m.p.: 215°–218° C. IR$\nu_{max}^{KBr}$ cm$^{-1}$: (—COO—) 1725 NMR (DMSO-d$_6$) δppm: 10.06–8.97 (4H, br) 8.90–7.21 (8H, m) 6.57 (1H, d, J=3.5 Hz) 4.39 (2H, d, J=5.9 Hz) 2.58–1.13 (8H, m)

EXAMPLE 24

6-Amidino-2-naphthyl 5-(6-carboxyhexanoylaminomethyl)furan-2-carboxylate hydrochloride m.p.: 199°–201° C. IR$\nu_{max}^{KBr}$ cm$^{-1}$: (—COO—) 1715 NMR (DMSO-d$_6$) δppm: 10.12–6.92 (12H, m) 6.57 (1H, d, J=3.5 Hz) 4.40 (2H, d, J=5.3 Hz) 2.63–0.48 (10H, m)

EXAMPLE 25

6-amidino-2-naphthyl 5-(7-carboxyheptanoylaminomethyl)furan-2-carboxylate hydrochloride m.p.: 179°–182° C. IR$\nu_{max}^{KBr}$ cm$^{-1}$: (—COO—) 1725, 1710 NMR (DMSO-d$_6$) δppm: 10.11–7.20 (12H, m) 6.57 (1H, d, J=3.5 Hz) 4.40 (2H, d, J=5.3 Hz) 2.65–0.71 (12H, m)

EXAMPLE 26

6-Amidino-2-naphthyl 5-(8-carboxyoctanoylaminomethyl)furan-2-carboxylate hydrochloride m.p.: 176°–181° C. IR$\nu_{max}^{KBr}$ cm$^{-1}$: (—COO—) 1735, 1710 NMR (DMSO-d$_6$) δppm: 11.98 (1H, brs) 10.02–9.07 (4H, br) 8.82–7.34 (8H, m) 6.56 (1H, d, J=3.5 Hz) 4.39 (2H, d, J=5.9 Hz) 2.46–0.82 (14H, m)

EXAMPLE 27

6-Amidino-2-naphthyl 5-(3-carboxypropionylaminomethyl)furan-2-carboxylate hydrobromide To 250 g of a 30% hydrobromic acid solution in acetic acid was added with water-cooling 8.0 g of 6-amidino-2-naphthyl 5-(3-t-butoxycarbonylpropionylaminomethyl)furan-2-carboxylate hydrobromide, and the mixture was stirred for 3 hours. The precipitate was filtered off, and the filtrate was poured into 2 l of ether. The mixture was stirred for 3 hours at room temperature and the precipitate was collected by filtration to obtain 5 g of the intended product.

m.p.: 218°–220° C.

In the same manner as in Example 27 but by using appropriate starting materials, the compounds of Examples 28 and 29 shown below were obtained.

EXAMPLE 28

6-amidino-2-naphthyl 5-(3-carboxypropionylaminomethyl)furan-2-carboxylate methanesulfonate m.p.: 175°–177° C. IR$\nu_{max}^{KBr}$ cm$^{-1}$: (—COO—) 1720 NMR (DMSO-d$_6$) δppm: 9.79–8.88 (4H, br) 8.74–7.37 (8H, m) 6.59 (1H, d, J=3.2 Hz) 4.40 (2H, d, J=4.7 Hz) 2.44 (4H, s) 2.40 (3H, s)

EXAMPLE 29

6-Amidino-2-naphthyl 5-(4-carboxy-2-guanidinobutyrylaminomethyl)furan-2-carboxylate dihydrobromide IR$\nu_{max}^{KBr}$ cm$^{-1}$: (—COO—) 1720 NMR (DMSO-d$_6$) δppm: 11.10–9.74 (1H, br) 9.65–6.80 (16H, m) 6.63 (1H, d, J=3.5 Hz) 4.67–4.12 (3H, m) 2.73–1.56 (4H, m)

EXAMPLE 30

6-amidino-2-naphthyl 5-(3-carboxypropionylaminomethyl)furan-2-carboxylate aluminium hydroxide hydrochloride In 1.84 l of 95% ethanol was dissolved 18.4 g of 6-amidino-2-naphthyl 5-(3-carboxypropionylaminomethyl)furan-2-carboxylate hydrochloride, and a solution of 8.42 g of aluminium isopropoxide in 670 ml of toluene was added dropwise thereto at room temperature. After completion of the addition, the reaction mixture was stirred for 3 hours and allowed to stand overnight. The crystals thus precipitated were collected by filtration to obtain 19.1 g of the intended product.

IR$\nu_{max}^{KBr}$ cm$^{-1}$: 3310 1724, 1632, 1560, 1518 1300, 1208, 1145

EXAMPLE 31

6-Amidino-2-naphthyl 5-(3-N,N-dimethylcarbamoylmethoxycarbonylpropionylaminomethyl)furan-2-carboxylate hydrochloride To 3.0 g of 3-N,N-dimethylcarbamoylmethoxycarbonylpropionic acid, 3.8 g of 6-amidino-2-naphthyl 5-aminomethylfuran-2-carboxylate dihydrochloride and 0.1 g of DMAP was added 30 ml of pyridine, and the mixture was stirred while cooling with ice. After 10 minutes, 6.2 g of DCC was added and the mixture was stirred for 3 hours while cooling with ice and then for 16 hours at room temperature. The precipitate was filtered off, the filtrate was added in small portions into 700 ml of ether and then the mixture was stirred for 30 minutes. The supernatant was decanted, 700 ml of acetone was added to the residue, then stirred for 1 hour and the supernatant was again removed by decantation. The residue was dissolved in 20 ml of methanol, 0.5 g of active carbon was added thereto, the mixture was stirred for 30 minutes while cooling with ice, and the insoluble was filtered off. The filtrate was added into 700 ml of acetone and stirred for 3 hours while cooling with ice. The precipitate was collected by filtration to obtain 1.4 g of the intended product.

IRv$_{max}^{KBr}$ cm$^{-1}$: (—COO—) 1730 NMR (DMSO-d$_6$) δppm: 10.03–9.07 (4H, br) 9.02–7.12 (8H, m) 6.65 (1H, d, J=3.5 Hz) 4.76 (2H, s) 4.41 (2H, d, J=5.6 Hz) 2.91 (3H, s) 2.81 (3H, s) 2.72–2.31 (4H, m)

In the same manner as in Example 31 but by using appropriate starting materials, the compounds of Examples 32 and 33 shown below were obtained.

EXAMPLE 32

6-Amidino-2-naphthyl 5-(3-carbamoylpropionylaminomethyl)furan-2-carboxylate hydrochloride m.p.: 205°–209° C. IRv$_{max}^{KBr}$ cm$^{-1}$: (—COO—) 1730, 1720 NMR (DMSO-d$_6$) δppm: 9.56 (4H, br) 8.88–6.14 (11H, m) 6.60 (1H, d, J=3.5 Hz) 4.39 (2H, d, J=5.6 Hz) 2.37 (4H, s)

EXAMPLE 33

6-Amidino-2-naphthyl 5-{[3-(4-methyl-1,3-dioxole-2-one-5-yl) methoxycarbonyl]propionylaminomethyl}furan-2-carboxylate hydrochloride m.p.: 126°–130° C. IRv$_{max}^{KBr}$ cm$^{-1}$: 1810, 1730 NMR (DMSO-d$_6$) δppm: 9.62 (4H, brs) 8.98–7.11 (8H, m) 6.58 (1H, d, J=3.5 Hz) 4.94 (2H, s) 4.39 (2H, d, J=5.6 Hz) 2.54 (4H, brs) 2.15 (3H, s)

EXAMPLE 34

6-Amidino-2-naphthyl 5-(3-methoxycarbonylpropionylaminomethyl)furan-2-carboxylate hydrochloride To a solution of 18 g of 6-amidino-2-naphthyl 5-aminomethylfuran-2-carboxylate dihydrochloride in 380 ml of DMF was added 19.1 ml of pyridine and then, while cooling with ice, 20 ml of a benzene solution containing 7.5 ml of 3-methoxycarbonylpropionyl chloride was added dropwise thereto for 20 minutes. After stirring at room temperature for 2.5 hours, the reaction mixture was added to 2 l of ether while stirring and cooling with ice, and the mixture was stirred at the same temperature for 5 hours. The supernatant was decanted and 1.5 l of ether was further added and stirred at room temperature for 18 hours. The precipitate was collected by filtration, 800 ml of acetone was added thereto, the mixture was stirred at room temperature for 5 hours, and the crystals were collected by filtration to obtain 19.6 g of the intended product.

m.p.: 198°–203° C. NMR (DMSO-d$_6$) δppm: 10.13–9.24 (4H, br) 9.02–7.39 (8H, m) 6.59 (1H, d, J=3.5 Hz) 4.41 (2H, d, J=5.6 Hz) 3.59 (3H, s) 2.52 (4H, s)

EXAMPLE 35

6-Amidino-2-naphthyl 5-(3-t-butoxycarbonylmethylcarbamoylpropionylaminomethyl)furan-2-carboxylate hydrochloride To 0.75 g of glycine t-butyl ester hydrochloride, 0.15 g of DMAP and 1.5 g of 6-amidino-2-naphthyl 5-(3-carboxypropionylaminomethyl)furan-2-carboxylate hydrochloride were added 20 ml of DMF and 1 ml of pyridine, and the mixture was stirred while cooling with ice. After 10 minutes, 0.9 g of DCC was added thereto, and the mixture was stirred for 3 hours while cooling with ice and then for 24 hours at room temperature. The precipitate was filtered off, the filtrate was added in small portions to 300 ml of ether, and the mixture was stirred at room temperature for 3 hours. The supernatant was decanted, then 200 ml of ether was added to the residue and stirred at room temperature for 19 hours. The precipitate was collected by filtration, then dissolved in 15 ml of methanol, 0.4 g of active carbon was added thereto and the mixture was stirred for 15 minutes while cooling with ice. The insoluble was filtered off, the filtrate was added to 200 ml of ether and the mixture was stirred for 5 hours while cooling with ice. The precipitate was collected by filtration to obtain 1.4 g of the intended product.

m.p.: 174°–176° C. NMR (DMSO-d$_6$) δppm: 10.11–9.19 (4H, br) 8.88–7.40 (9H, m) 6.59 (1H, d, J=3.5 HZ) 4.40 (2H, d, J=5.3 HZ) 3.70 (2H, d, J=3.7 HZ) 2.42 (4H, s) 1.40 (9H, s)

EXAMPLE 36

6-Amidino-2-naphthyl 5-(3-carboxymethylcarbamoylpropionylaminomethyl) furan-2-carboxylate hydrochloride In 35 ml of acetic acid and 3 ml of DMF was dissolved 1.3 g of 6-amidino-2-naphthyl 5-(3-t-butoxycarbonylmethylcarbamoylpropionylaminomethyl)furan-2 -carboxylate hydrochloride, and hydrogen chloride gas was passed into the solution for 1 hour while cooling with ice.

The reaction mixture was stirred for 2 hours with ice-cooling and then for 18 hours with water-cooling, then the insoluble was filtered off, the filtrate was added to 300 ml of ether and the mixture was stirred for 3 hours at room temperature. The supernatant was decanted, 200 ml of acetone was added to the residue and the mixture was stirred for 18 hours at room temperature. The precipitate was collected by filtration to obtain 1.1 g of the intended product.

m.p.: 217°–218° C. NMR (DMSO-d$_6$) δppm: 10.03–9.17 (4H, br) 8.92–7.32 (9H, m) 6.61 (1H, d, J=3.2 Hz) 4.60–4.10 (2H, m) 3.76 (2H, d, J=5.4 Hz) 2.44 (4H, s)

The same intended product can be also obtained in the following manner. In 35 ml of DMF was dissolved 4 g of the compound of Example 46, then 0.7 g of 5% palladium-carbon was added thereto, and the mixture was subjected to catalytic reduction at room temperature. After 15 hours, the insoluble was filtered off, the filtrate was added slowly to 400 ml of ether, and the mixture was stirred for 3 hours while cooling with ice. The supernatant was decanted, then 1 ml of concentrated hydrochloric acid and 200 ml of ether were added to the residue and stirred for 15 hours while cooling with water. The supernatant was decanted, 200 ml of acetone was added to the residue and the mixture was stirred for 3 hours at room temperature. The precipitate was collected by filtration to obtain 3.1 g of the intended product.

In the same manner as in Example 21 but by using appropriate starting materials, the respective compounds of Examples 37 to 39 shown below were obtained.

EXAMPLE 37

6-Amidino-2-naphthyl 5-(2-carboxypropionylaminomethyl)furan-2-carboxylate hydrochloride m.p.: 236°–239° C. IRv$_{max}^{KBr}$ cm$^{-1}$: (—COO—) 1723 NMR (DMSO-d$_6$) δppm: 10.14–9.09 (4H, br) 9.06–7.32 (8H, m) 6.58 (1H, d, J=3.5 Hz) 4.39 (2H, d, J=5.3 Hz) 2.51–1.85 (1H, m) 1.43–0.77 (3H, m)

EXAMPLE 38

6-Amidino-2-naphthyl 5-(2-carboxybutyrylaminomethyl)furan-2-carboxylate hydrochloride m.p.: 225°–228° C. IR$\nu_{max}^{KBr}$ cm$^{-1}$: (—COO—) 1725 NMR (DMSO-$d_6$) δppm: 10.15–9.10 (4H, br) 9.04–7.24 (8H, m) 6.57 (1H, d, J=3.5 Hz) 4.40 (2H, d, J=5.9 Hz) 2.36–0.65 (6H, m)

EXAMPLE 39

6-Amidino-2-naphthyl 5-[2-carboxy-2-methylpropionylaminomethyl)furan-2-carboxylate hydrochloride m.p.: 216°–220° C. IR$\nu_{max}^{KBr}$ cm$^{-1}$: (—COO—) 1733 NMR (DMSO-$d_6$) δppm: 10.06–9.09 (4H, br) 8.88–7.33 (8H, m) 6.54 (1H, d, J=3.5 Hz) 4.39 (2H, d, J=5.9 Hz) 1.10 (3H, s) 0.98 (3H, s)

EXAMPLE 40

6-Amidino-2-naphthyl 5-[(1-carboxycyclopropan-1-yl)carbonylaminomethyl]furan-2-carboxylate methanesulfonate In the same manner as in Example 21 but by using an appropriate starting material, 6-amidino-2-naphthyl 5-[(1-carboxycyclopropan-1-yl)carbonylaminomethyl]furan-2-carboxylate hydrochloride was obtained. Then, 0.5 g of the hydrochloride obtained above was dissolved in 3 ml of DMF, and 0.33 ml of triethylamine was added thereto while cooling with ice and stirring. The reaction mixture was stirred for 2 hours while cooling with ice and for 15 hours while cooling with water. The precipitate was collected by filtration, washed with 5 ml of water and dried. Thereafter, 1 ml of DMF and 0.05 g of methanesulfonic acid were added to dissolve the crystals, and 50 ml of ether was added to the solution while stirring and cooling with ice.

After 2 hours, the supernatant was decanted, 70 ml of ether was further added to the residue and the mixture was stirred for 3 hours while cooling with water. The crystals were collected by filtration and washed with 20 ml of ether to obtain 0.16 g of the intended product.

NMR (DMSO-$d_6$) δppm: 9.95–8.84 (5H, m) 8.77–7.29 (7H, m) 6.59 (1H, d, J=3.2 Hz) 4.51 (2H, d, J=4.9 Hz) 2.41 (3H, s) 1.41 (4H, s)

EXAMPLE 41

6-Amidino-2-naphthyl 5-(3-carboxy-2,3-dimethylpropionylaminomethyl)furan-2-carboxylate hydrochloride To 2.3 g of 2,3-dimethylsuccinic acid, 2.0 g of -amidino-2-naphthyl 5-aminomethylfuran-2-carboxylate dihydrochloride and 66 mg of DMAP was added 25 ml of pyridine, and the mixture was stirred while cooling with ice. After 10 minutes, 2.16 g of DCC was added and the mixture was stirred for 1 hour at 4°–8° C. and then for 2 hours at 16°–17° C. The precipitate was filtered off, the filtrate was added in small portions into 150 ml of ether and the mixture was stirred for 1 hour at room temperature. The precipitate was collected by filtration, then 60 ml of acetone was added thereto and the mixture was stirred for 3 hours. The precipitate was collected by filtration to obtain 1.3 g of the intended product.

m.p.: 145° C. (d) IR$\nu_{max}^{KBr}$ cm$^{-1}$: (—COO—) 1720 NMR (DMSO-$d_6$) δppm: 12.58–11.87 (1H, br) 10.15–9.00 (4H, br) 8.94–7.30 (8H, m) 6.57 (1H, d, J=3.2 Hz) 4.43 (2H, d, J=4.4 Hz) 2.97–2.24 (2H, m) 1.09 (6H, d, J=4.7 Hz)

EXAMPLE 42

6-Amidino-2-naphthyl 5-[(2-carboxy-trans-DL-cyclopentan-1-yl)carbonylaminomethyl]furan-2-carboxylate hydrochloride To 60 ml of pyridine were added 1.9 g of 6-amidino-2-naphthyl 5-aminomethylfuran-2-carboxylate dihydrochloride, 3.9 g of trans-DL-1,2-cyclopentanedicarboxylic acid and 60 mg of DMAP, then, while stirring and cooling with ice, 1.5 g of DCC was added and the mixture was stirred for 24 hours. The precipitate was filtered off and the filtrate was added dropwise into 700 ml of ether. The supernatant was decanted, the residue was dissolved in 70 ml of DMF, and 3.4 ml of triethylamine was added to the solution while stirring and cooling with ice. After stirring for 1 hour, 40 ml of water was added and the mixture was stirred for 10 minutes. The precipitate was collected by filtration, washed with small amounts of water and acetone, and air-dried. Then, 50 ml of acetone was added to the dried product, 1 ml of concentrated hydrochloric acid was further added with ice-cooling and stirring, then, 10 minutes later, 150 ml of ether was added and the mixture was stirred for 24 hours. The precipitate was collected by filtration to obtain 1.5 g of the intended product as a white solid.

m.p.: 151° C. ~(d) IR$\nu_{max}^{KBr}$ cm$^{-1}$: (—COO—) 1710 NMR (DMSO-$d_6$) δppm: 10.06–9.01 (4H, br) 8.94–7.29 (8H, m) 6.54 (1H, d, J=3.5 Hz) 4.40 (2H, d, J=4.7 Hz) 2.97 (2H, brs) 1.71 (6H, brs)

EXAMPLE 43

In the same manner as in Example 21 but by using an appropriate starting material, the following compound was obtained.

6-Amidino-2-naphthyl 5-(4-carboxy-3-methylbutyrylaminomethyl)furan-2-carboxylate hydrochloride m.p.: 180°–181° C. IR$\nu_{max}^{KBr}$ cm$^{-1}$: (—COO—) 1720 NMR (DMSO-$d_6$) δppm: 10.32–9.05 (4H, br) 9.05–7.23 (8H, m) 6.57 (1H, d, J=3.5 Hz) 4.40 (2H, d, J=5.0 Hz) 2.77–1.71 (5H, m) 0.91 (3H, d, J=4.4 Hz)

EXAMPLE 44

In the same manner as in Example 42 but by using an appropriate starting material, the following compound was obtained.

6-amidino-2-naphthyl 5-(4-carboxy-3-cyclopentylidenebutyrylaminomethyl)furan-2-carboxylate hydrochloride m.p.: 180°–184° C. IR$\nu_{max}^{KBr}$ cm$^{-1}$: (—COO—) 1735 (sch) 1724 NMR (DMSO-$d_6$) δppm: 12.06 (1H, brs) 10.11–8.96 (4H, br) 8.93–7.20 (8H, m) 6.56 (1H, d, J=3.5 Hz) 4.41 (2H, d, J=4.6 Hz) 2.44 (2H, s) 2.38 (2H, s) 1.57 (8H, s)

EXAMPLE 45

In the same manner as in Example 40 but by using an appropriate starting material, the following compound was obtained.

6-Amidino-2-naphthyl 5-(4-carboxy-3-cyclohexylidenebutyrylaminomethyl)furan-2-carboxylate methanesulfonate.

IRv$_{max}^{KBr}$ cm$^{-1}$: (—COO—) 1740, 1710 NMR (DMSO-d$_6$) δppm: 9.77–8.85 (4H, br) 8.71–7.50 (8H, m) 6.58 (1H, d, J=3.2 Hz) 4.45 (2H, d, J=3.5 Hz) 2.64–1.94 (7H, m) 1.43 (10H, br)

EXAMPLE 46

6-Amidino-2-naphthyl 5-(3-benzyloxycarbonylmethylcarbamoylpropionylaminomethyl)furan-2-carboxylate hydrochloride The intended compound was obtained in the same manner as in Example 35 but by using an appropriate starting material.

NMR (DMSO-d$_6$) δppm: 9.81–9.03 (4H, br) 8.78–6.94 (14H, m) 6.59 (1H, d, J=3.2 Hz) 5.12 (2H, s) 4.20 (2H, d, J=4.9 Hz) 3.90 (2H, d, J=5.6 Hz ) 2.44 (4H, s)

EXAMPLE 47

6-Amidino-2-naphthyl 5-(4-carboxybutyrylaminomethyl)furan-2-carboxylate methanesulfonate To 10 ml of DMF was added 2.0 g of 6-amidino-2-naphthyl 5-(4-carboxybutyrylaminomethyl)furan-2-carboxylate hydrochloride, then 4.6 g of methanesulfonic acid was added dropwise while cooling with ice, and the mixture was stirred for 10 minutes. Then, the mixture was added in small portions into 400 ml of acetone and stirred for 4 hours while cooling with ice. The supernatant was decanted, 1 l of ether was added to the residue and stirred, and the precipitate was collected by filtration to obtain 1.54 g of the intended product.

m.p.: 181°–184° C. IRv$_{max}^{KBr}$ cm$^{-1}$: (—COO—) 1725 NMR (DMSO-d$_6$) δppm: 10.40–8.86 (4H, br) 8.80–7.18 (8H, m) 6.57 (1H, d, J=3.5 Hz) 4.44 (2H, d, J=5.6 Hz) 2.59–1.38 (9H, m)

EXAMPLE 48

In the same manner as in Example 47 but by using an appropriate starting material, the following compound was obtained.

6-Amidino-2-naphthyl 5-carboxyacetylaminomethylfuran-2-carboxylate methanesulfonate m.p.: 171°–172° C. IRv$_{max}^{KBr}$ cm$^{-1}$: (—COO—) 1740 NMR (DMSO-d$_6$) δppm: 12.55 (1H, brs) 9.78–8.97 (4H, br) 8.94–7.09 (8H, m) 6.63 (1H, d, J=3.5 Hz) 4.44 (2H, d, J=5.9 Hz) 3.24 (1H, s) 2.09 (3H, s)

EXAMPLE 49

In the same manner as in Example 31 but by using an appropriate starting material, the following compound was obtained.

6-amidino-2-naphthyl 5-(4-carbamoylbutyrylaminomethyl)furan-2-carboxylate hydrochloride m.p.: 193°–196° C. IRv$_{max}^{KBr}$ cm$^{-1}$: (—COO—) 1730 NMR (DMSO-d$_6$) δppm: 10.46–8.93 (4H, br) 9.07–5.99 (11H, m) 4.40 (2H, d, J=5.3 Hz) 2.58–1.34 (6H, m)

EXAMPLE 50

6-amidino-2-naphthyl 5-(19-carboxynonadecanoylaminomethyl)furan-2-carboxylate hydrochloride The title compound was obtained in the same manner as in Example 42 but by using an appropriate starting material.

m.p.: 188°–191° C. IRv$_{max}^{KBr}$ cm$^{-1}$: (—COO—) 1738 NMR (DMSO-d$_6$) δppm: 9.85–9.30 (4H, br) 8.63 (1H, brs) 8.56 (1H, t, J=5.6 Hz) 8.32–8.11 (2H, m) 8.07–7.92 (2H, m) 7.73–7.52 (2H, m) 6.57 (1H, d, J=3.3 Hz) 4.40 (2H, d, J=5.6 Hz) 2.27–2.11 (4H, m) 1.63–1.39 (4H, m) 1.22 (28H, brs)

Japanese Priority Application 04-023848 filed on Feb. 10, 1992, is relied on and incorporated by reference.

Table 4 shows the structural formulas of the products obtained in the Examples described above.

TABLE 4

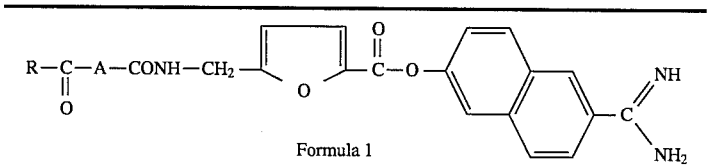

Formula 1

| Example No. | Structural Formula | |
|---|---|---|
| | R | A |
| 1 | H$_3$C—C(CH$_3$)(CH$_3$)—O— | —CH=CH—⟨phenyl⟩— |
| 2 | HO— | —CH=CH—⟨phenyl⟩— |

TABLE 4-continued
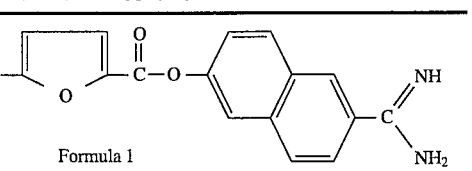
Formula 1
| Example No. | Structural Formula R | A |
|---|---|---|
| 3 | HO— | ⟨C₆H₄⟩ |
| 4 | H₃CO— | —CH₂—⟨C₆H₄⟩— |
| 5 | H₃C—C(CH₃)₂—O— | —⟨C₆H₄⟩—CH₂— |
| 6 | HO— | —⟨C₆H₄⟩—CH₂— |
| 7 | HO— | —CH₂—⟨C₆H₄⟩— |
| 8 | HO— | —⟨C₆H₄⟩—CH=CH— |
| 9 | HO— | —CH₂—CH—⟨C₆H₄⟩— |
| 10 | HO— | ⟨cyclohexyl⟩ |
| 11 | HO— | ⟨cyclohexyl⟩ |
| 12 | HO— | cis CH=CH |
| 13 | HO— | trans CH=CH |
| 14 | H₃C—C(CH₃)₂—O— | — |
| 15 | H₃C—C(CH₃)₂—O— | —CH₂— |
| 16 | HO— | — |
| 17 | HO— | —CH₂— |

TABLE 4-continued

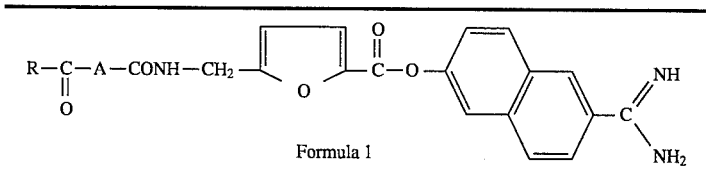

Formula 1

| Example No. | R | A |
|---|---|---|
| 18 | H₃C—C(CH₃)(CH₃)—O— | —CH₂—CH₂— |
| 19 | H₃C—C(CH₃)(CH₃)—O— | —CH₂—CH₂—CH₂— |
| 20 | H₃C—C(CH₃)(CH₃)—O— | —CH₂—CH₂—CH—<br>NH—C(=NH)NH₂ |
| 21 | HO— | —CH₂—CH₂— |
| 22 | HO— | —(CH₂)₃— |
| 23 | HO— | —(CH₂)₄— |
| 24 | HO— | —(CH₂)₅— |
| 25 | HO— | —(CH₂)₆— |
| 26 | HO— | —(CH₂)₇— |
| 27 | HO— | —CH₂—CH₂— |
| 28 | HO— | —CH₂—CH₂— |
| 29 | HO— | —CH₂—CH₂—CH—<br>NH—C(=NH)NH₂ |
| 30 | (HO)₂AlO— | —CH₂—CH₂— |
| 31 | (H₃C)₂N—C(=O)—CH₂O— | —CH₂—CH₂— |
| 32 | H₂N— | —CH₂—CH₂— |
| 33 | (cyclic carbonate with H₃C and CH₂—O—) | —CH₂—CH₂— |
| 34 | H₃C—O— | —CH₂—CH₂— |
| 35 | H₃C—C(CH₃)(CH₃)—O— | —CH₂NHCOCH₂CH₂— |
| 36 | HO— | —CH₂NHCOCH₂CH₂— |
| 37 | HO— | —CH(CH₃)— |
| 38 | HO— | —CH(CH₂CH₃)— |

TABLE 4-continued

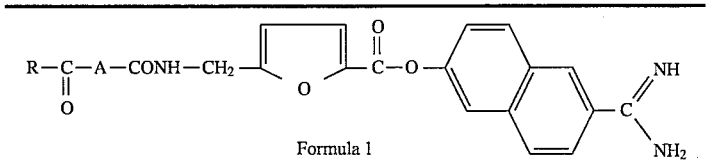

Formula 1

| Example No. | Structural Formula R | A |
|---|---|---|
| 39 | HO— | —C(CH₃)(CH₃)— |
| 40 | HO— | cyclopropylidene (gem-disubstituted cyclopropane) |
| 41 | HO— | —CH(CH₃)—CH(CH₃)— |
| 42 | HO— | trans-1,2-cyclopentylene |
| 43 | HO— | —CH₂—CH(CH₃)—CH₂— |
| 44 | HO— | —CH₂—(1,1-cyclopentylene)—CH₂— |
| 45 | HO— | —CH₂—(1,1-cyclohexylene)—CH₂— |
| 46 | C₆H₅—CH₂O— | —CH₂NHCOCH₂CH₂ |
| 47 | HO— | —(CH₂)₃— |
| 48 | HO— | —CH₂— |
| 49 | H₂N— | —(CH₂)₃— |
| 50 | HO— | —(CH₂)₁₈— |

What is claimed:

1. An amidinonaphthyl furancarboxylate derivative of the formula I

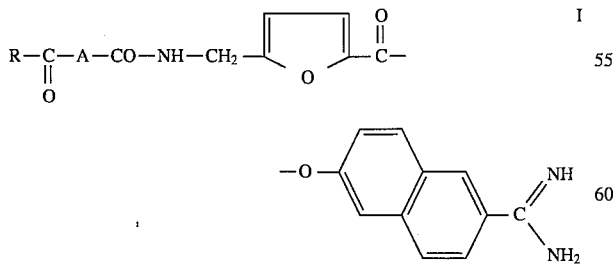

wherein A is a single bond or A denotes (a) a phenyl group, cyclopentyl group, or cyclohexyl group, (b) an alkenylphenyl group, alkylphenyl group, phenylalkenyl group, or phenylalkyl group wherein alkyl is $C_1$ to $C_7$ alkyl and alkenyl is $C_2$ to $C_7$ alkenyl, (c) a $C_1$ to $C_{18}$ alkyl or $C_2$ to $C_7$ alkenyl group which may be substituted by one or two substituents selected from $C_1$ to $C_5$ alkyl groups and quanidino groups, wherein an alkyl substituent together with the carbon atom to which it is attached may form a cycloalkyl ring having from 3 to 6 carbon atoms, or said $C_1$ to $C_5$ alkyl may itself be substituted by a $C_3$ to $C_6$ cycloalkyl ring, or (d) —(CH₂)$_n$—NH—CO—(CH₂)$_{n'}$· wherein n and n' may be the same or different and represent an integer from 1 to 4; and wherein R denotes (e) a hydroxyl group, (f) a $C_1$ to $C_7$ alkoxy group which may be mono- or disubstituted by $C_1$ to $C_5$ alkyl, (g) a phenyl-$C_{1-C_4}$alkoxy group, (h) —OAl(OH)$_2$,
(i) an amino group,
(j)

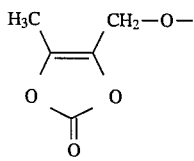

or
(k)

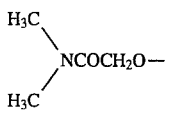

or a pharmaceutically acceptable addition salt thereof.

2. The amidinonaphthyl furancarboxylate derivative according to claim 1 wherein, in the formula I, A is an $C_2$–$C_7$ alkenylphenyl group and R is a hydroxyl group or a $C_1$–$C_7$ alkoxy group which may be mono- or disubstituted by $C_1$ to $C_5$ alkyl.

3. The amidinonaphthyl furancarboxylate derivative according to claim 1 wherein, in the formula I, A is a phenyl-$C_1$–$C_7$alkyl group and R is a hydroxyl group or a $C_1$ to $C_7$ alkoxy group which may may be mono- or disubstituted by $C_1$ to $C_5$ alkyl.

4. The amidinonaphthyl furancarboxylate derivative according to claim 1 wherein, in the formula I, A is a $C_1$ to $C_{18}$ alkyl or $C_2$ to $C_7$ alkenyl group which may be substituted by one or two substituents selected from $C_1$ to $C_5$ alkyl groups and guanidino groups, wherein an alkyl substituent wherein an alkyl substituent together with the carbon atom to which it is attached may form a cycloalkyl ring having from 3 to 6 carbon atoms, or said $C_1$ to $C_5$ alkyl may itself be substituted by a $C_3$ to $C_6$ cycloalkyl ring, and R is a hydroxyl group, a $C_1$ to $C_7$ alkoxy group which may be mono- or disubstituted by $C_1$ to $C_5$ alkyl, —OAl(OH)$_2$, an amino group,

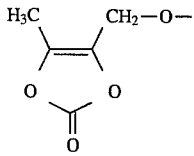

or

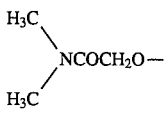

5. The amidinonaphthyl furancarboxylate derivative according to claim 1 wherein, in the formula I, A is an $C_1$–$C_7$ alkylphenyl group and R is a hydroxyl group or a $C_1$ to $C_7$ alkoxy group which may be mono- or di-substituted by $C_1$ to $C_5$ alkyl groups.

6. The amidinonaphthyl furancarboxylate derivative according to claim 1 wherein, in the formula I, A is a phenyl group and R is a hydroxyl group.

7. The amidinonaphthyl furancarboxylate derivative according to claim 1 wherein, in the formula I, A is a phenyl-$C_1$–$C_7$alkenyl group and R is a hydroxyl group.

8. The amidinonaphthyl furancarboxylate derivative according to claim 1 wherein, in the formula I, A is a cyclopenty or cyclohexyl group and R is a hydroxyl group.

9. The amidinonaphthyl furancarboxylate derivative according to claim 1 wherein, in the formula I, A is a —(CH$_2$)$_n$—NH—CO—(CH$_2$)$_{n'}$ wherein n and n' may be the same or different and represent an integer from 1 to 4 and R is a hydroxyl group, a $C_1$ to $C_7$ alkoxy group which may be mono- or disubstituted by $C_1$ to $C_5$ alkyl, or a phenyl-$C_1$–$C_4$alkoxy group.

10. The amidinonaphthyl furancarboxylate derivative according to claim 1 wherein, in the formula I, A is a single bond and R is a hydroxyl group or a $C_1$ to $C_7$ alkoxy group which may be mono- or disubstituted by $C_1$ to $C_5$ alkyl.

11. The amidinonaphthyl furancarboxylate derivative according to claim 1, wherein A is a $C_1$ to $C_{18}$ alkyl group and R is a hydroxyl group, amino group or $C_1$ to $C_7$ alkoxy group.

12. The amidinonaphthyl furancarboxylate derivative according to claim 1 which is 6-Amidino-2-naphthyl 5-(4-carboxyphenylacetyl-aminomethyl)furan-2-carboxylate hydrochloride.

13. The amidinonaphthyl furancarboxylate derivative according to claim 1 which is 6-Amidino-2-naphthyl 5-(trans-4-carboxy-1-cyclohexanoylaminomethyl)furan-2-carboxylate hydrochloride.

14. The amidinonaphthyl furancarboxylate derivative according to claim 1 which is 6-Amidino-2-naphthyl 5-(trans-2-carboxyvinyl)-carbonylaminomethylfuran-2-carboxylate hydrochloride.

15. The amidinonaphthyl furancarboxylate derivative according to claim 1 which is 6-Amidino-2-naphthyl 5-carboxyacetylaminomethylfuran-2-carboxylate hydrochloride.

16. The amidinonaphthyl furancarboxylate derivative according to claim 1 which is 6-Amidino-2-naphthyl 5-(3-carboxypropionylaminomethyl)furan-2-carboxylate hydrochloride.

17. The amidinonaphthyl furancarboxylate derivative according to claim 1 which is 6-Amidino-2-naphthyl 5-(4-carboxybutyrylaminomethyl)furan-2-carboxylate hydrochloride.

18. The amidinonaphthyl furancarboxylate derivative according to claim 1 which is 6-Amidino-2-naphthyl 5-(5-carboxyvalerylaminomethyl)furan-2-carboxylate hydrochloride.

19. The amidinonaphthyl furancarboxylate derivative according to claim 1 which is 6-Amidino-2-naphthyl 5-(8-carboxyoctanoylaminomethyl)furan-2-carboxylate hydrochloride.

20. The amidinonaphthyl furancarboxylate derivative according to claim 1 which is 6-Amidino-2-naphthyl 5-(3-carbamoylpropionylaminomethyl)furan-2-carboxylate hydrochloride.

21. The amidinonaphthyl furancarboxylate derivative according to claim 1 which is 6-Amidino-2-naphthyl 5-(3-methoxycarbonylpropionylaminomethyl)furan-2-carboxylate hydrochloride.

22. The amidinonaphthyl furancarboxylate derivative according to claim 1 which is 6-Amidino-2-naphthyl 5-(3-carboxymethylcarbamoylpropionylaminomethyl)furan-2-carboxylate hydrochloride.

23. The amidinonaphthyl furancarboxylate derivative according to claim 1 which is 6-Amidino-2-naphthyl 5-(2-carboxybutyrylaminomethyl)furan-2-carboxylate hydrochloride.

24. The amidinonaphthyl furancarboxylate derivative according to claim 1, wherein said derivative is 6-Amidino-2-naphthyl 5-(4-(2-t-butoxycarbonylvinyl)benzoylaminomethyl)furan-2-carboxylate hydrobromide;

6-Amidino-2-naphthyl 5-(4-(2-carboxyvinyl)benzoylaminomethyl)furan-2-carboxylate hydrochloride;

6-Amidino-2-naphthyl 5-(4-carboxybenzoylaminomethyl)furan-2-carboxylate hydrochloride;

6-Amidino-2-naphthyl 5-(4-methoxycarbonylmethylbenzoylaminomethyl)furan-2-carboxylate hydrochloride;

6-Amidino-2-naphthyl 5-(4-t-butoxycarbonylphenylacetylaminomethyl)furan-2-carboxylate hydrochloride;

6-Amidino-2-naphthyl 5-(4-carboxyphenylacetylaminomethyl)furan-2-carboxylate hydrochloride;

6-Amidino-2-naphthyl 5-(4-carboxymethylbenzoylaminomethyl)furan-2-carboxylate hydrochloride;

6-Amidino-2-naphthyl 5-(4-carboxycinnamoylaminomethyl)furan-2-carboxylate hydrochloride;

6-Amidino-2-naphthyl 5-(4-(2-carboxyethyl)benzoylaminomethyl)furan-2-carboxylate hydrochloride;

6-Amidino-2-naphthyl 5-(cis-4-carboxy-1-cyclohexanoylaminomethyl)furan-2-carboxylate hydrochloride;

6-Amidino-2-naphthyl 5-(trans-4-carboxy-1-cyclohexanoylaminomethyl)furan-2-carboxylate hydrochloride;

6-Amidino-2-naphthyl 5-(cis-2-carboxyvinyl)carbonylaminomethylfuran-2-carboxylate methanesulfonate;

6-Amidino-2-naphthyl 5-(trans-2-carboxyvinyl)carbonylaminomethylfuran-2-carboxylate hydrochloride;

6-Amidino-2-naphthyl 5-t-butoxyoxalylaminomethylfuran-2-carboxylate hydrochloride;

6-Amidino-2-naphthyl 5-t-butoxymalonylaminomethylfuran-2-carboxylate hydrochloride;

6-Amidino-2-naphthyl 5-oxaloaminomethylfuran-2-carboxylate hydrochloride;

6-Amidino-2-naphthyl 5-carboxyacetylaminomethylfuran-2-carboxylate hydrochloride;

6-Amidino-2-naphthyl 5-(3-t-butoxycarbonylpropionylaminomethyl)furan-2-carboxylate hydrochloride;

6-Amidino-2-naphthyl 5-(4-t-butoxycarbonylbutyrylaminomethyl)furan-2-carboxylate hydrochloride;

6-Amidino-2-naphthyl 5-(4-t-butoxycarbonyl-2-guanidinobutyrylaminomethyl)furan-2-carboxylate hydrochloride hydrobromide;

6-Amidino-2-naphthyl 5-(3-carboxypropionylaminomethyl)furan-2-carboxylate hydrochloride;

6-Amidino-2-naphthyl 5-(4-carboxybutyrylaminomethyl)furan-2-carboxylate hydrochloride;

6-Amidino-2-naphthyl 5-(5-carboxyvalerylaminomethyl)furan-2-carboxylate hydrochloride;

6-Amidino-2-naphthyl 5-(6-carboxyhexanoylaminomethyl)furan-2-carboxylate hydrochloride;

6-Amidino-2-naphthyl 5-(7-carboxyheptanoylaminomethyl)furan-2-carboxylate hydrochloride;

6-Amidino-2-naphthyl 5-(8-carboxyoctanoylaminomethyl)furan-2-carboxylate hydrochloride;

6-Amidino-2-naphthyl 5-(3-carboxypropionylaminomethyl)furan-2-carboxylate hydrochloride;

6-Amidino-2-naphthyl 5-(3-carboxypropionylaminomethyl)furan-2-carboxylate methanesulfonate;

6-Amidino-2-naphthyl 5-(4-carboxy-2-guanidinobutyrylaminomethyl)furan-2-carboxylate dihydrobromide;

6-Amidino-2-naphthyl 5-(3-carboxypropionylaminomethyl)furan-2-carboxylate aluminum hydroxide hydrochloride;

6-Amidino-2-naphthyl 5-(3-N,N-dimethylcarbamoylmethoxycarbonylpropionylaminomethyl)furan-2-carboxylate hydrochloride;

6-Amidino-2-naphthyl 5-(3-carbamoylpropionylaminomethyl)furan-2-carboxylate hydrochloride;

6-Amidino-2-naphthyl 5-((3-(4-methyl-1,3-dioxole-2-one-5-yl)methoxycarbonyl)propionylaminomethyl)furan-2-carboxylate hydrochloride;

6-Amidino-2-naphthyl 5-(3-methoxycarbonylpropionylaminomethyl)furan-2-carboxylate hydrochloride;

6-Amidino-2-naphthyl 5-(3-t-butoxycarbonylmethylcarbamoylpropionylaminomethyl)furan-2-carboxylate hydrochloride;

6-Amidino-2-naphthyl 5-(3-carboxymethylcarbamoylpropionylaminomethyl)furan-2-carboxylate hydrochloride;

6-Amidino-2-naphthyl 5-(2-carboxypropionylaminomethyl)furan-2-carboxylate hydrochloride;

6-Amidino-2-naphthyl 5-(2-carboxybutyrylaminomethyl)furan-2-carboxylate hydrochloride;

6-Amidino-2-naphthyl 5-(2-carboxy-2-methylpropionylaminomethyl)furan-2-carboxylate hydrochloride;

6-Amidino-2-naphthyl 5-((1-carboxycyclopropan-1-yl)carbonylaminomethyl)furan-2-carboxylate methanesulfonate;

6-Amidino-2-naphthyl 5-(3-carboxy-2,3-dimethylpropionylaminomethyl)furan-2-carboxylate hydrochloride;

6-Amidino-2-naphthyl 5-((2-carboxy-trans-DL-cyclopentan-1-yl)carbonylaminomethyl)furan-2-carboxylate hydrochloride;

6-Amidino-2-naphthyl 5-(4-carboxy-3-methylbutyrylaminomethyl)furan-2-carboxylate hydrochloride;

6-Amidino-2-naphthyl 5-(4-carboxy-3-cyclopentylidenebutyrylaminomethyl)furan-2-carboxylate hydrochloride;

6-Amidino-2-naphthyl 5-(4-carboxy-3-cyclohexylidenebutyrylaminomethyl)furan-2-carboxylate methanesulfonate;

6-Amidino-2-naphthyl 5-(3-benzyloxycarbonylmethylcarbamoylpropionylaminomethyl)furan-2-carboxylate hydrochloride;

6-Amidino-2-naphthyl 5-(4-carboxybutyrylaminomethyl)furan-2-carboxylate methanesulfonate;

6-Amidino-2-naphthyl 5-carboxyacetylaminomethylfuran-2-carboxylate methanesulfonate;

6-Amidino-2-naphthyl 5-(4-carbamoylbutyrylaminomethyl)furan-2-carboxylate hydrochloride; or 6-Amidino-2-naphthyl 5-(19-carboxynonadecanoylaminomethyl)furan-2-carboxylate hydrochloride.

25. A pharmaceutical preparation comprising the derivative or the acid addition salt thereof according to claim 1 in combination with at least one pharmaceutically acceptable carrier.

26. The pharmaceutical composition according to claim 25, wherein, in the formula I, A is an $C_2$–$C_7$ alkenylphenyl group and R is a hydroxyl group or a $C_1$–$C_7$ alkoxy group which may be mono- or disubstituted by $C_1$ to $C_5$ alkyl.

27. The pharmaceutical composition according to claim 25, wherein, in the formula I, A is a phenyl-$C_1$–$C_7$alkyl group and R is a hydroxyl group or a $C_1$ to $C_7$ alkoxy group which may may be mono- or disubstituted by $C_1$ to $C_5$ alkyl.

28. The pharmaceutical composition according to claim 25, wherein, in the formula I, A is a $C_1$ to $C_{18}$ alkyl or $C_2$ to $C_7$ alkenyl group which may be substituted by one or two substituents selected from $C_1$ to $C_5$ alkyl groups and guanidino groups, wherein an alkyl substituent wherein an alkyl substituent together with the carbon atom to which it is attached may form a cycloalkyl ring having from 3 to 6 carbon atoms, or said $C_1$ to $C_5$ alkyl may itself be substituted by a $C_3$ to $C_6$ cycloalkyl ring, and R is a hydroxyl group, a $C_1$ to $C_7$ alkoxy group which may be mono- or disubstituted by $C_1$ to $C_5$ alkyl, $-OAl(OH)_2$, an amino group,

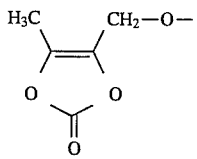

or

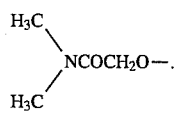

29. The pharmaceutical composition according to claim 25, wherein, in the formula I, A is an $C_1$-$C_7$ alkylphenyl group and R is a hydroxyl group or a $C_1$ to $C_7$ alkoxy group which may be mono- or di-substituted by $C_1$ to $C_5$ alkyl groups.

30. The pharmaceutical composition according to claim 25, wherein, in the formula I, A is a phenyl group and R is a hydroxyl group.

31. The pharmaceutical composition according to claim 25, wherein, in the formula I, A is a phenyl-$C_2$-$C_7$alkenyl group and R is a hydroxyl group.

32. The pharmaceutical composition according to claim 25, wherein, in the formula I, A is a cyclopenty or cyclohexyl group and R is a hydroxyl group.

33. The pharmaceutical composition according to claim 25, wherein, in the formula I, A is a $-(CH_2)_n-NH-CO(CH_2)_{n'}$ wherein n and n' may be the same or different represent an integer from 1 to 4 and R is a hydroxyl group, a $C_1$ to $C_7$ alkoxy group which may be mono- or disubstituted by $C_1$ to $C_5$ alkyl, or a phenyl-$C_1$-$C_4$alkoxy group.

34. The pharmaceutical composition according to claim 25, wherein, in the formula I, A is a single bond and R is a hydroxyl group or a $C_1$ to $C_7$ alkoxy group which may be mono- or disubstituted by $C_1$ to $C_5$ alkyl.

35. The pharmaceutical composition according to claim 25, wherein A is a $C_1$ to $C_{18}$ alkyl group and R is a hydroxyl group, amino group or $C_1$ to $C_7$ alkoxy group.

36. The pharmaceutical composition according to claim 25, wherein said pharmaceutical composition is in the form of tablets, capsules, troches, powders, pills, granules, suppositories, ointments, creams, syrups, elixirs, lyophilized products, solutions or suspensions.

37. The pharmaceutical composition according to claim 25, further comprising at least one additive selected from the following:

(a) a binder selected from the group consisting of gum arabic, gelatin, sorbitol, tragacanth, poly(vinyl pyrrolidone), poly(vinyl alcohol), hydroxypropyl methyl cellulose, crystalline cellulose, sodium carboxymethyl cellulose, and mixtures thereof;

(b) a vehicle selected from the group consisting of lactose, sucrose, mannitol, corn starch, calcium phosphate, sorbitol, vegetable oil, polyethylene glycol, crystalline cellulose, and mixtures thereof;

(c) a lubricant selected from the group consisting of magnesium stearate, talc, polyethylene glycol, silica, and mixtures thereof;

(d) a disintegrator selected from the group consiting of potato starch, hydroxypropyl cellulose, calcium carboxymethyl cellulose, sodium carboxymethyl starch, and mixtures thereof;

(e) a suspending agent selected from the group consisting of methyl cellulose, sodium carboxymethyl cellulose, hydroxypropyl cellulose, hydroxypropyl methyl cellulose, poly(vinyl pyrrolidone) poly(vinyl alcohol), tragachanth, gelatin, sodium alginate, and mixtures thereof;

(f) an emulsifier selected from the group consisting of lecithin, sorbitan, fatty acid esters, gum arabic, tragacanth, and mixtures thereof;

(g) a wetting agent selected from the group consisting of polyoxyethylene sorbitan fatty acid esters, polyoxyethylene fatty acid esters, hydrogenated castor oil, sesame oil, soybean oil, propylene glycol, polyethylene glycol, ethyl alcohol, and mixtures thereof;

(h) an antiseptic selected from the group consising of methyl p-hydroxybenzoate, propyl p-hydroxybenzoate, sorbic acid, and mixtures thereof;

(i) a sweetner selected from the group consisting of simple syrups, sucrose, sorbitol, mannitol, and mixtures thereof;

(j) an oily base selected from the group consisting of cacao butter, Witepsol, triglyceride, and mixtures thereof;

(k) a water-soluble base selected from the group consisting of glycerol, glycerogelatin, Macrogol, and mixtures thereof; and (l) a surfactant.

38. A method of treating nephritis, said method comprising administering to a mammal in need thereof an effective amount of the pharmaceutical composition according to claim 25, said ammount being effective in treating nephritis.

39. The method according to claim 38, said amount being 30 mg/kg body weight of said mammal.

40. The method according to claim 38, said amount being 1 to 400 mg administered 1 to 4 times a day.

41. A method of treating arthritis, said method comprising administering to a mammal in need thereof an effective amount of the pharmaceutical composition according to claim 25, said ammount being effective in treating arthritis.

42. The method according to claim 41, said amount being 30 to 60 mg/kg body weight of said mammal.

43. The method according to claim 41, said amount being 1 to 400 mg administered 1 to 4 times a day.

44. A method of at least partially inhibiting the in vitro activity of trypsin, plasmin, thrombin, kallikrein and/or complement, said method comprising adding to a sample an effective amount of the amidinonaphthyl furancarboxylate derivative according to claim 1, said ammount being effective in inhibiting trypsin, plasmin, thrombin, kallikrein and/or complement.

\* \* \* \* \*